(12) United States Patent
Katou et al.

(10) Patent No.: US 10,531,911 B2
(45) Date of Patent: Jan. 14, 2020

(54) MEDICAL DEVICE

(71) Applicant: TERUMO KABUSHIKI KAISHA, Shibuya-ku (JP)

(72) Inventors: Yukitoshi Katou, Hadano (JP); Hiromitsu Hashimoto, Hadano (JP); Hiromu Sugiyama, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 500 days.

(21) Appl. No.: 14/224,930

(22) Filed: Mar. 25, 2014

(65) Prior Publication Data

US 2014/0324038 A1 Oct. 30, 2014

Related U.S. Application Data

(63) Continuation of application No. PCT/JP2012/073365, filed on Sep. 12, 2012.

(30) Foreign Application Priority Data

Sep. 26, 2011 (JP) ................................. 2011-208628

(51) Int. Cl.
*A61B 18/14* (2006.01)
*A61B 18/12* (2006.01)
*A61B 18/00* (2006.01)

(52) U.S. Cl.
CPC ...... *A61B 18/1477* (2013.01); *A61B 18/1206* (2013.01); *A61B 18/1492* (2013.01);
(Continued)

(58) Field of Classification Search
CPC .. A61B 2018/0038; A61B 2018/00351; A61B 18/085; A61B 18/1477
See application file for complete search history.

(56) References Cited

U.S. PATENT DOCUMENTS 5,308,358 A 5/1994 Bond et al.
7,326,221 B2 * 2/2008 Sakamoto .......... A61B 17/0469
606/139
(Continued)

FOREIGN PATENT DOCUMENTS

EP 1 584 295 A2 10/2005
JP 2005-296645 A 10/2005
(Continued)

OTHER PUBLICATIONS

International Search Report (PCT/ISA/210) dated Oct. 9, 2012, by the Japanese Patent Office as the International Searching Authority for International Application No. PCT/JP2012/073365.
(Continued)

*Primary Examiner* — Michael F Peffley
*Assistant Examiner* — Bo Ouyang
(74) *Attorney, Agent, or Firm* — Buchanan Ingersoll & Rooney PC

(57) ABSTRACT

A medical device that can perform plural actions by a single operation and is excellent in operability includes a catheter that is insertable into a living body, a sandwiching portion and a needle positioning portion that are disposed in the catheter so as to be able to advance and retract. A slide portion is operable such that the sandwiching portion and the needle positioning portion advance and retract simultaneously, and an action switching portion causes the sandwiching portion to advance and retract in tandem with or independently of the slide portion by the advance and retraction of the slide portion.

20 Claims, 22 Drawing Sheets

(52) U.S. Cl.
CPC ............. *A61B 2018/0038* (2013.01); *A61B 2018/0063* (2013.01)

(56) References Cited

U.S. PATENT DOCUMENTS

| | | |
|---|---|---|
| 2005/0131396 A1 | 6/2005 | Stanczak et al. |
| 2005/0288688 A1 | 12/2005 | Sakamoto et al. |
| 2008/0086153 A1 | 4/2008 | Sakamoto et al. |
| 2009/0069810 A1* | 3/2009 | Kuroda ............. A61B 17/0057 606/51 |
| 2009/0069844 A1 | 3/2009 | Green et al. |
| 2010/0152732 A1* | 6/2010 | Katou ............... A61B 18/1492 606/49 |
| 2012/0310227 A1 | 12/2012 | Katou |

FOREIGN PATENT DOCUMENTS

| | | |
|---|---|---|
| JP | 2009-233020 A | 10/2009 |
| JP | 2011-19763 A | 2/2011 |
| WO | WO 2011/111410 A1 | 9/2011 |

OTHER PUBLICATIONS

The extended European Search Report dated Oct. 12, 2015, by the European Patent Office in corresponding European Patent Application No. 12835809.0-1659 (6 pgs).

\* cited by examiner

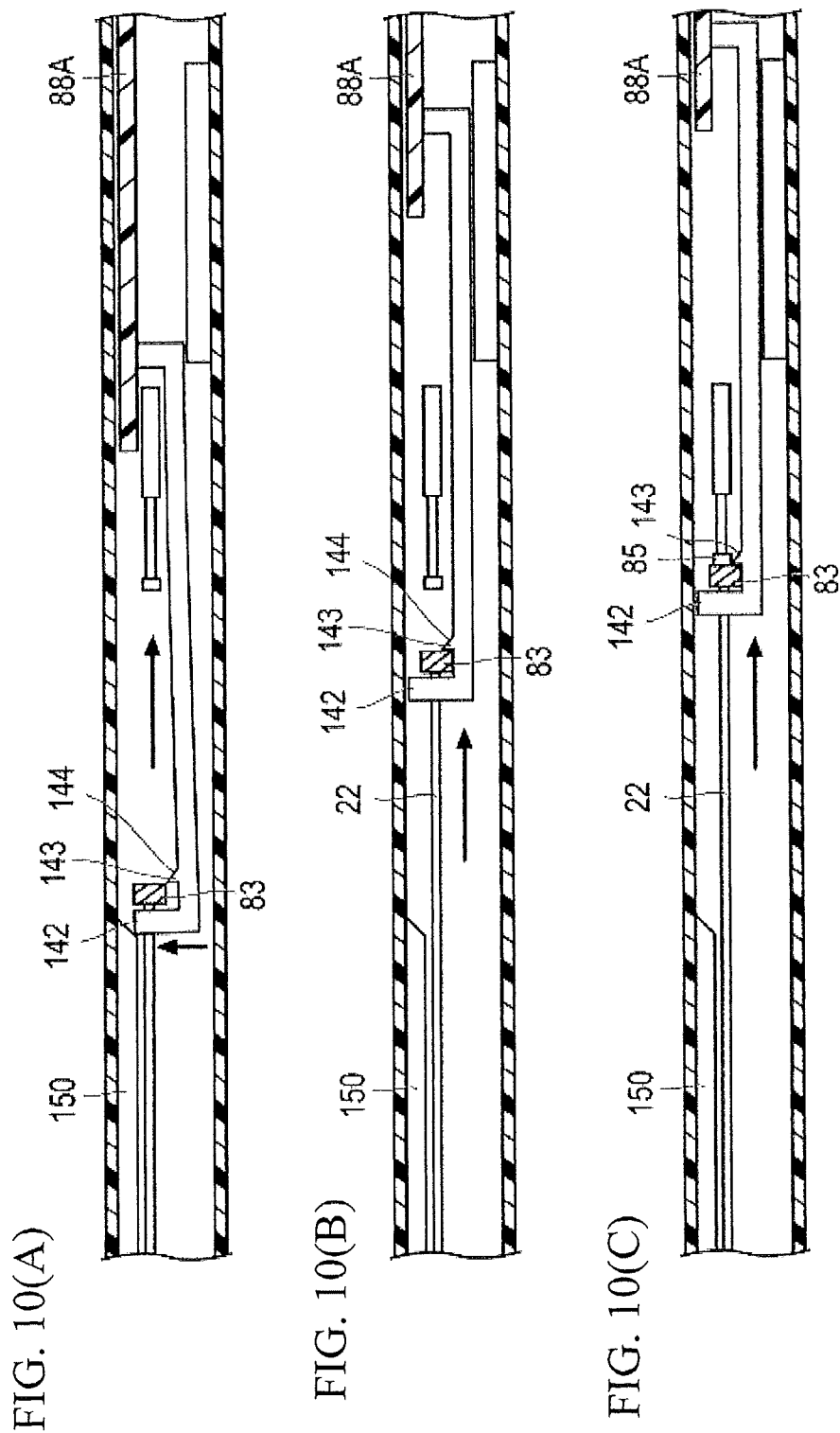

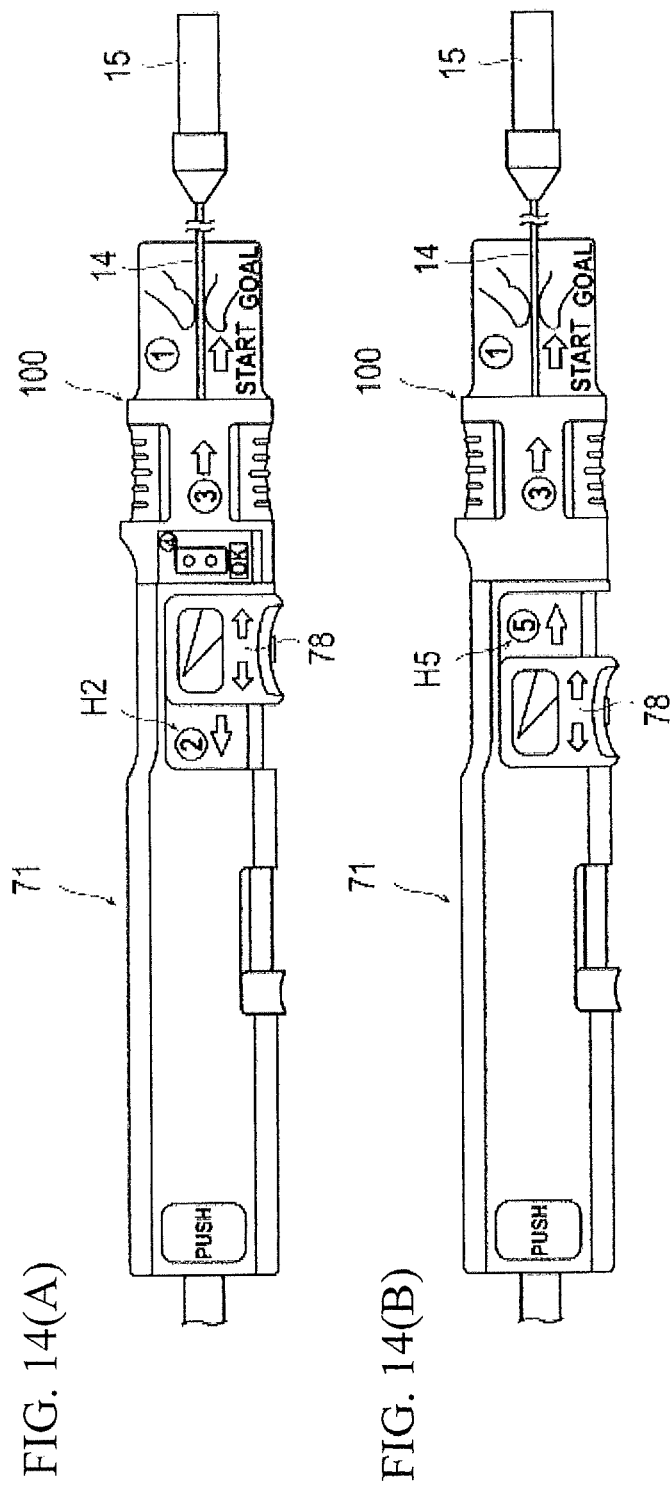

MEDICAL DEVICE

CROSS REFERENCES TO RELATED APPLICATION

This application is a continuation of International Application No. PCT/JP2012/073365 filed on Sep. 21, 2012, and claims priority to Japanese Application No. 2011-208628 filed on Sep. 26, 2011, the entire content of both of which is incorporated herein by reference.

TECHNICAL FIELD

The present invention relates to a medical device and method, particularly to a medical device inserted into a body lumen and a method that involves using a medical device.

BACKGROUND DISCUSSION

Recently, Patent Foramen Ovale (hereinafter, abbreviated to PFO) has been identified as a cardiogenic factor responsible for stroke and migraine. PFO is a symptom caused when the foramen ovale, which causes right-to-left cardiac shunt in infancy, remains in the body even after the infant has grown up. It is reported that 20% to 30% of adults suffer from PFO.

The foramen ovale is formed in the Septum Secundum (hereinafter, described as "atrial septum secundum") of the heart. Ordinarily, since the left atrial pressure is higher than the right atrial pressure in the heart, the left atrium is closed by the Septum Primum (hereinafter, described as a "foramen ovale valve"). However, when the right atrial pressure becomes higher than the left atrial pressure due to tension (for example, coughing or firmly maintaining posture) or the like, the foramen ovale opens toward the left atrium, whereby the blood flows into the left atrial side (arterial side) from the right atrial side (venous side). If the blood contains thrombi, the thrombi move to the arterial side from the venous side. The thrombi then move to the left atrium, the left ventricle, the aorta, and the brain in this order and become a factor responsible for stroke, migraine, and the like.

If percutaneous catheterization, which is conducted as a procedure for addressing the aforementioned disease, can produce the same effects as produced by open-heart surgery, this procedure is regarded as a desirable method.

Devices for closing surgery using percutaneous catheters can also be used for closing defects such as congenital atrial septal defect (ASD), PFO, ventricular septal defect (VSD), and patent ductus arteriosus (PDA). However, the devices used in the conventional procedure clamp the foramen ovale and the atrial septum secundum by using a disk-like membrane or an anchoring member for closing the defects and are allowed to indwell the body.

The body considers the membrane or anchoring member a foreign substance, and thrombi easily adhere thereto. Particularly, after adhering to the disk-like membrane of the left atrial side, the thrombi may move and cause a stroke and may break the thin foramen ovale. Moreover, the position of these members may not be fixed in a state of clamping the defect, and the members may stray from their position.

Accordingly, recently, a PFO closure device which sandwiches the foramen ovale and the atrial septum secundum between a pair of electrodes and applies electric energy from both the electrodes to connect tissues has been proposed. An example is disclosed in Japanese Application Publication No. 2009-233020. With this PFO closure device, biological tissue is held by a positioning member that protrudes from a catheter, a sticking member consisting of the pair of electrodes and a sandwiching member are then used to stick the sticking member into the foramen ovale valve, the foramen ovale valve and the atrial septum secundum are then sandwiched between the sticking member and the sandwiching member, and electric energy is applied to the biological tissue to connect the tissues. If such a device having the simple constitution as above is used, it is possible to reliably connect the foramen ovale to the atrial septum secundum by a simple procedure without causing a foreign substance to indwell the body.

Moreover, the device has a structure in which the positioning member, the sandwiching member, and the sticking member are individually operated at the operator's side of the device.

The aforementioned PFO closure device has a structure in which the positioning member, the sandwiching member, and the sticking member are individually operated at the operator's side of the device. Accordingly, the operation thereof is complicated.

SUMMARY

One aspect of the disclosure here involves a medical device comprised of a cylindrical body configured to be inserted into a living body; at least two shaft portions movably positioned in the cylindrical body and configured to move relative to the cylindrical body to undergo advancing and retracting movement; an operation unit configured to operate the at least two shaft portions such that the shaft portions advance and retract simultaneously; and an action switching portion configured to make at least one of the shaft portions which advances and retracts in tandem with the advance and retraction of the operation unit to advance and retract independently of the advance and retraction of the operation unit.

The medical device also includes an operation unit that can operate the at least two shaft portions such that the shaft portions advance and retract simultaneously, and an action switching portion that makes at least one of the shaft portions advance and retract in tandem with or independently of the operation unit when the operation unit advances and retracts. Accordingly, plural shaft portions performing different actions can be operated by only operating one operation unit, whereby the operability is improved.

Due to the operation of the operation unit, at least one of the shaft portions is interlocked with or separated from the operation unit by the action switching portion. It is preferable for the shaft portion to advance and retract in tandem with or independently of the operation unit in this manner. In this case, if a structure by which the shaft portion is interlocked with or separated from the operation unit is used, it is possible to effectively cause the shaft to advance and retract in tandem with or independently of the operation unit.

It is preferable for the medical device to include a needle portion that is an electrode configured to be stuck into biological tissue around a defect present in the biological tissue. The shaft portion that advances and retracts in tandem with or independently of the operation unit by the action switching portion is preferably a sandwiching portion as an electrode which enables the biological tissue to be sandwiched between the sandwiching portion and the needle portion and enables electric currents to flow between the sandwiching portion and the needle portion. The other shaft portion that is not the sandwiching portion is preferably a positioning portion which is attached to the biological tissue and positions at least one of the needle portion and the sandwiching portion in the biological tissue. In this case, the sandwiching portion and the positioning portion performing different actions can be operated simply by operating a single operation unit, whereby it is possible to improve the operability when a defect present in the biological tissue is closed by electric currents.

The sandwiching portion may include a sandwiching shaft configured to protrude from the cylindrical body and a proximal member that is disposed at the proximal side of the sandwiching shaft and moves into contact with a member for supplying electric currents. It is preferable for the action switching portion to include an interlock member that moves along with the operation unit while being interlocked with the operation unit and is separably interlocked with the proximal member. In this case, it is possible to switch actions of the sandwiching portion by using the proximal member necessary for applying electric currents, without separately providing other members.

It is also preferable for the action switching portion to include a deformation inducing portion that deforms the interlock member by bumping into or contacting the interlock member, which moves by a push-in operation of the operation unit, to separate the interlock member having been interlocked with the proximal member. It is thus possible to deform the interlock member by using the push-in operation of the operation unit and to effectively switch the actions of the sandwiching portion.

The action switching portion preferably causes the sandwiching portion to independently move in a state where both the sandwiching portion and the positioning portion advance by the push-in operation of the operation unit, and preferably causes the sandwiching portion to move in tandem with the retracting positioning portion in a state where the positioning portion is retracting by the pull-back operation of the operation unit such that both the sandwiching portion and the positioning portion retract. The positioning portion is thus operated in a wide range and the sandwiching portion operated in a narrow range can be operated by a single operation unit, hence the operability is improved.

It is preferable for the shaft portion, which advances and retracts in tandem with or independently of the operation unit by the action switching portion, to be able to advance and retract by another operation member different from the operation unit. With this construction, the shaft portion that independently advances and retracts can be individually operated, hence the operability is improved.

According to another aspect, a medical device that is positionable in a living body to correct a defect in biological tissue in the living body includes a catheter main body configured to be inserted into a living body, and a clamp to clamp a portion of the biological tissue, wherein the clamp includes a needle configured to puncture the biological tissue and a sandwiching member that, together with the needle, sandwiches the portion of the biological tissue. The medical device also includes an elongated tube positioned in the catheter main body and axially movable relative to the catheter main body, and an operation unit that is manually operable to undergo axial movement, with the operation unit being connected to the elongated tube so that the elongated tube moves together with the operation unit whenever the operation unit axially moves through manual operation of the operation unit. An action switching portion is operatively located between the operation unit and the sandwiching member, and the action switching portion is configured to movably link the operation unit and the sandwiching member so that the sandwiching member moves together with the operation unit during the axial movement of the operation unit, the action switching portion being configured to separate the operation unit from the sandwiching member so that the operation unit axially moves independent of the sandwiching member.

Another aspect involves a method comprising positioning a medical device in a living body, wherein the medical device includes: a catheter main body configured to be inserted into a living body; a clamp to clamp a portion of the biological tissue, the clamp including a sandwiching portion; an elongated tube positioned in the catheter main body and axially movable relative to the catheter main body; and an operation unit that is manually operable to undergo axial movement. The method also involves axially moving the operation unit which is operatively connected to both the sandwiching portion and the elongated tube to axially move both the sandwiching portion and the elongated tube together with the operation unit, disconnecting the operative connection between the operation unit and the sandwiching portion while maintaining the operative connection between the operation unit and the elongated tube, and further axially moving the operation unit after the operative disconnection of the sandwiching portion from the operation unit so that the further axial movement of the operation unit axially moves the elongated tube without axially moving the sandwiching portion.

The medical device and method disclosed here which makes it possible to perform plural actions by a single operation and exhibits excellent operability.

BRIEF DESCRIPTION OF THE DRAWING FIGURES

Figure 7:
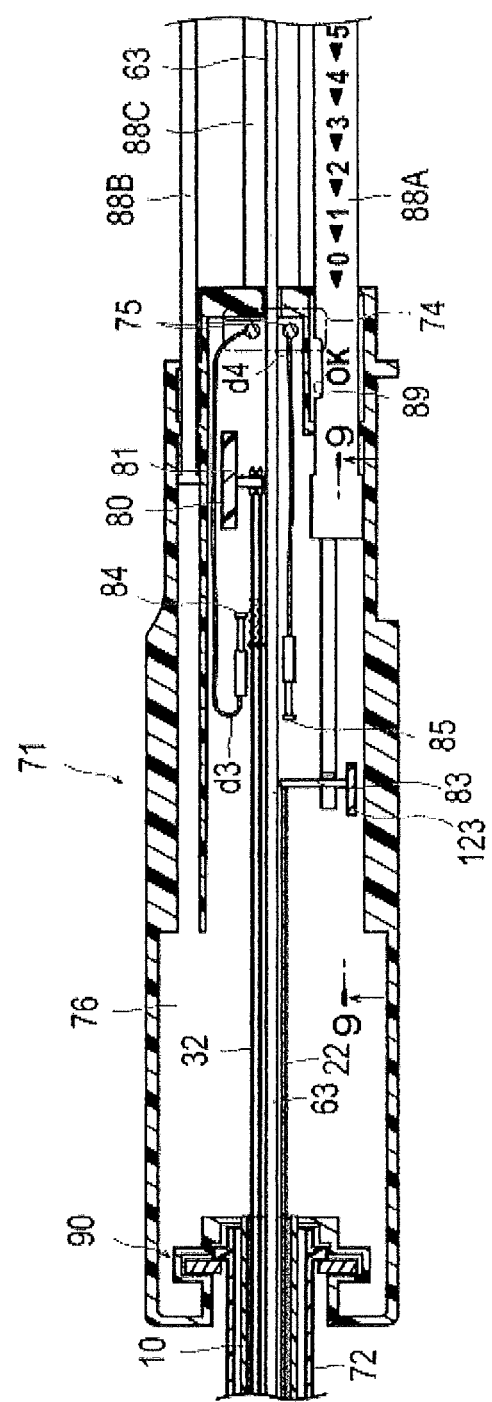
FIG. 7 is a cross-sectional view of the operation unit at the operator's side taken along the section line 7-7 in FIG. 2.
Figure 9A:
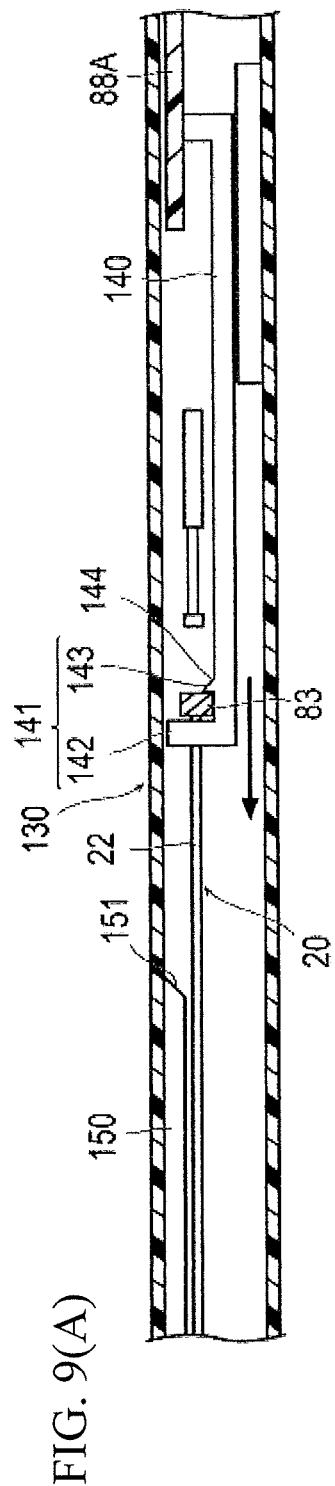
Figure 9B:
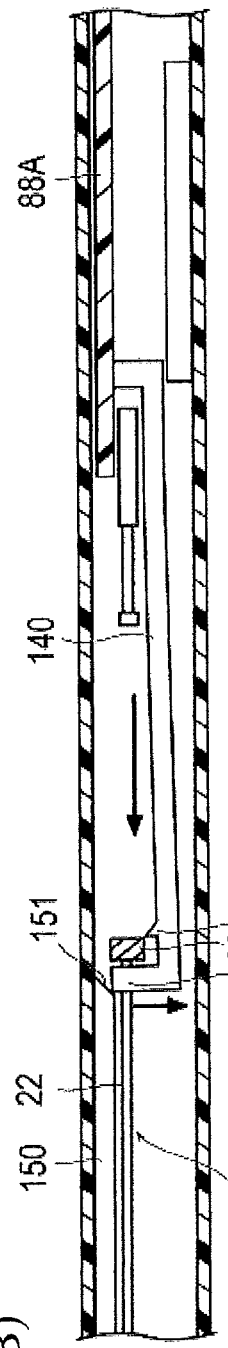
Figure 9C:
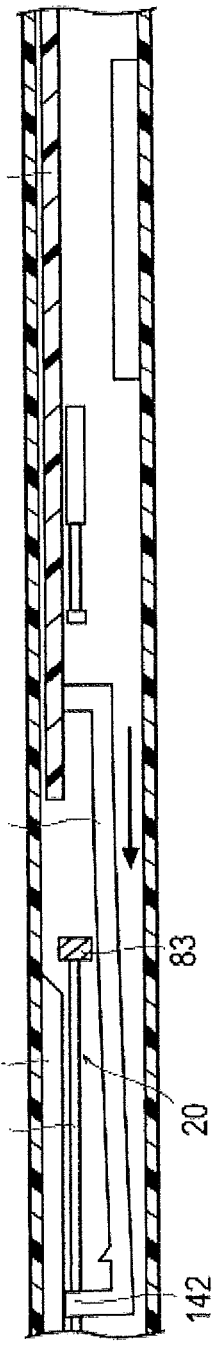

FIGS. 9(A)-9(C) are cross-sectional views of the operation unit at the operator's side taken along the section line 9-9 in FIG. 7 showing a state where a slide portion is caused to advance, with FIG. 9(A) showing a state (interlock state) where an interlock member has not yet come into contact with a deformation inducing portion, FIG. 9(B) showing a state where the interlock portion comes into contact with the deformation inducing portion, and FIG. 9(C) showing a state (separate state) where the interlock member has come into contact with the deformation inducing portion.

FIGS. 10(A)-(C) are cross-sectional views of the operation unit at the operator's side taken along the section line 9-9 in FIG. 7 and showing a state where the slide portion is caused to retract, with FIG. 10(A) showing a state where the interlock member has reached the proximal side of the deformation inducting portion, FIG. 10(B) showing a state where the interlock member has reached a proximal side away from the deformation inducting portion, and FIG. 10(C) showing a state where a terminal has come into contact with a contact member. This is an enlarged cross-sectional view of the operation unit at the operator's side in a state of causing the slide portion to retract.

Figure 6:
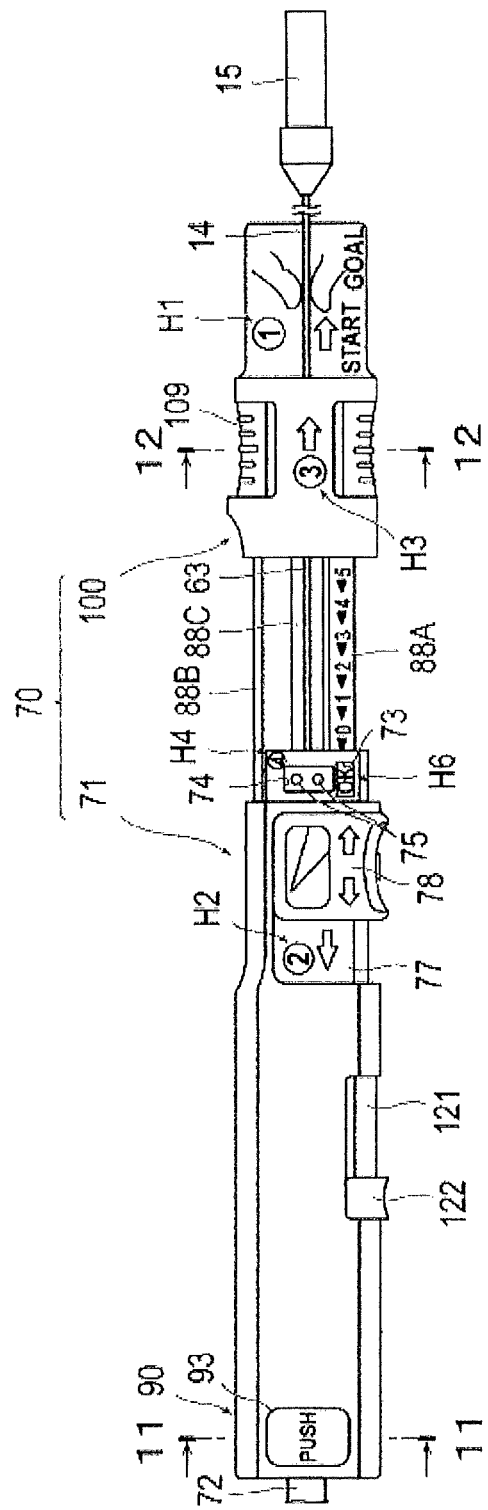
FIG. 6 is a plan view showing an operation unit at the operator's side of the medical device according to the present embodiment.
Figure 11:
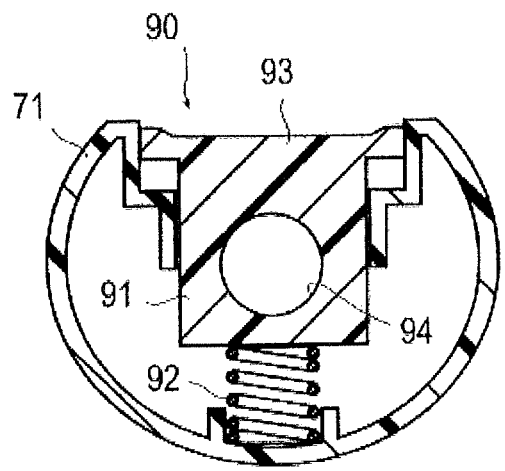

FIG. 11 is a cross-sectional view showing an interlock mechanism taken along the section line 11-11 in FIG. 6.

Figure 12:
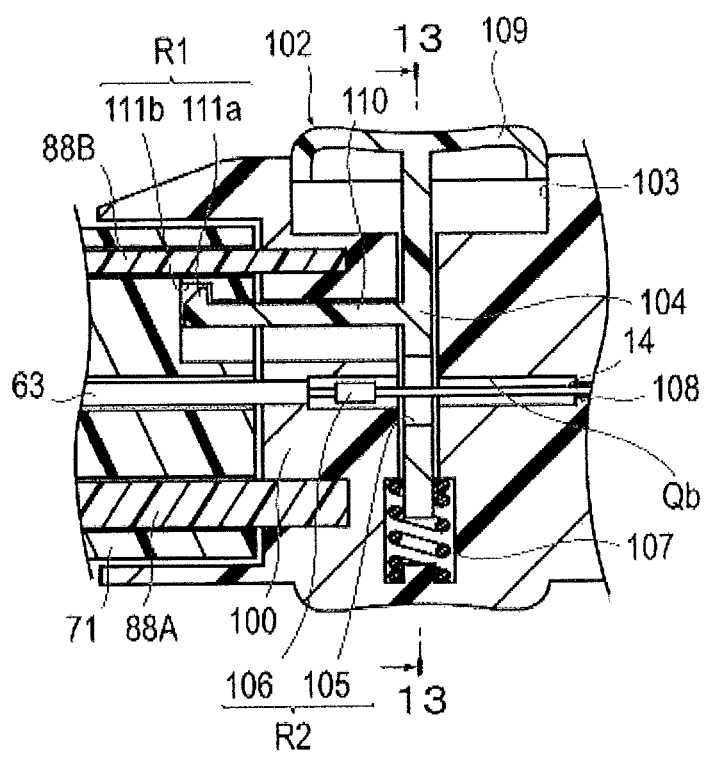

FIG. 12 is a cross-sectional view of a lock-unlock mechanism portion taken along the section line 12-12 in FIG. 6.

Figure 13:
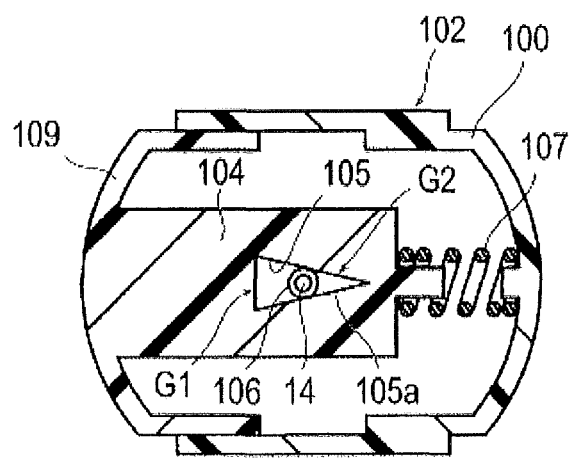

FIG. 13 is a cross-sectional view taken along the section line 13-13 in FIG. 12.

FIGS. 14(A) and (B) are plan views showing the operation unit at the operator's side in a state of operating a needle operating lever, with FIG. 14(A) showing a state before the operation, and FIG. 14(B) showing a state after the operation.

Figure 15A:
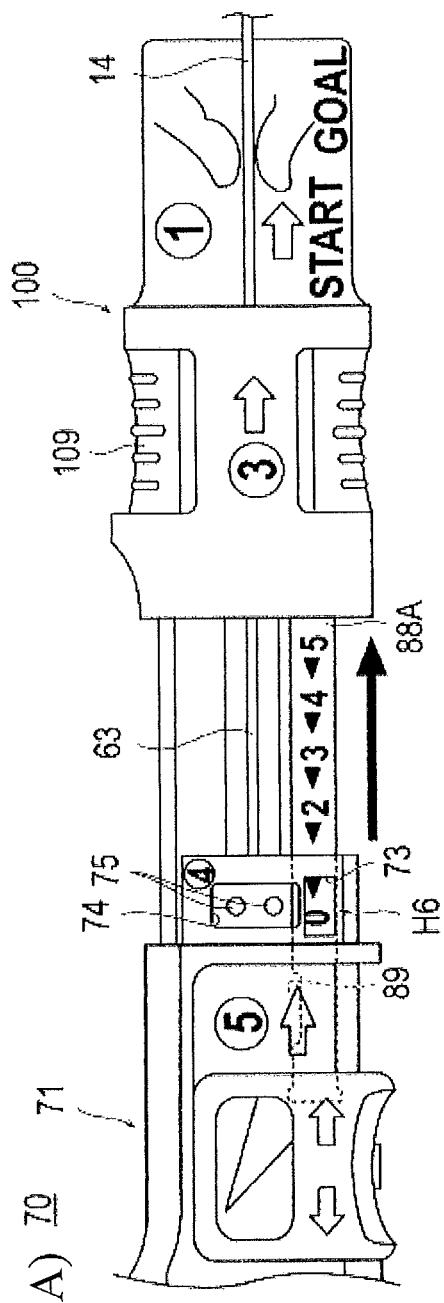
Figure 15B:
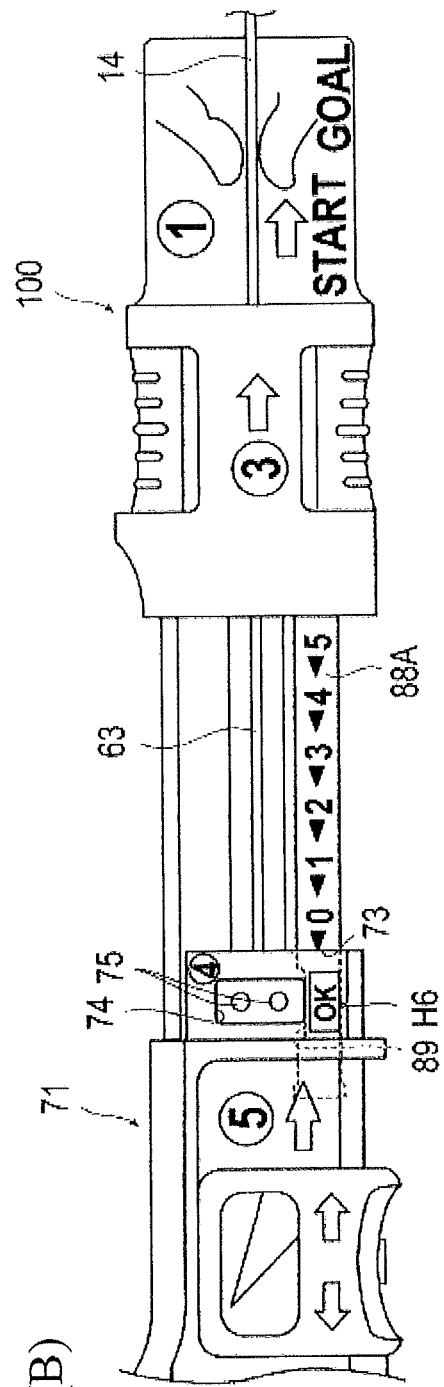

FIGS. 15(A) and (B) are enlarged plan views showing the operation unit at the operator's side in a state of causing the slide portion to retract, wherein FIG. 15(A) shows a state during the retraction, and FIG. 15(B) shows a state after the retraction.

Figure 16:
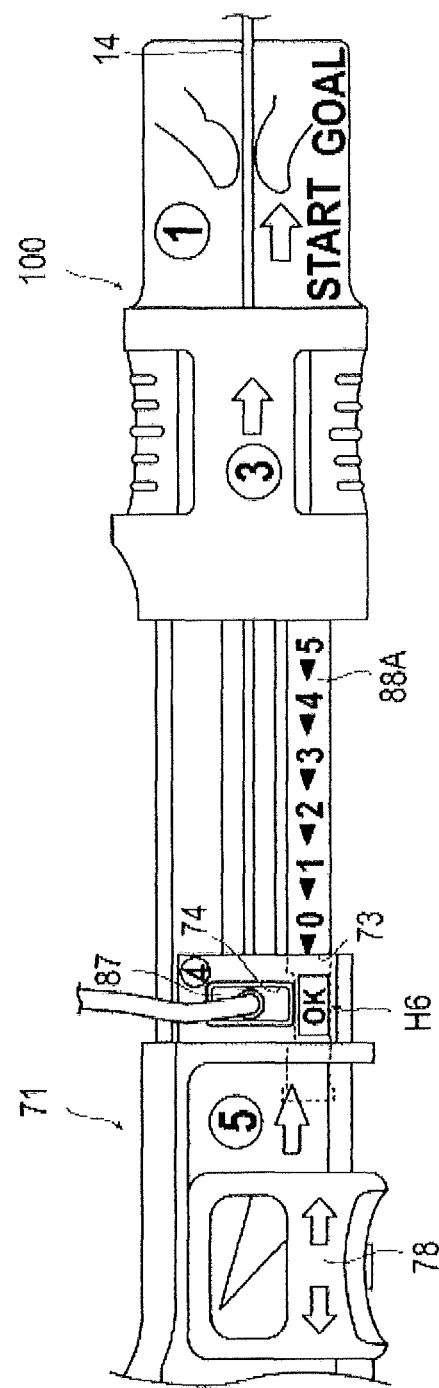

FIG. 16 is an enlarged plan view showing the operation unit at the operator's side in a state where an output connector has been connected to an input connector of the operation unit at the operator's side.

Figure 17:
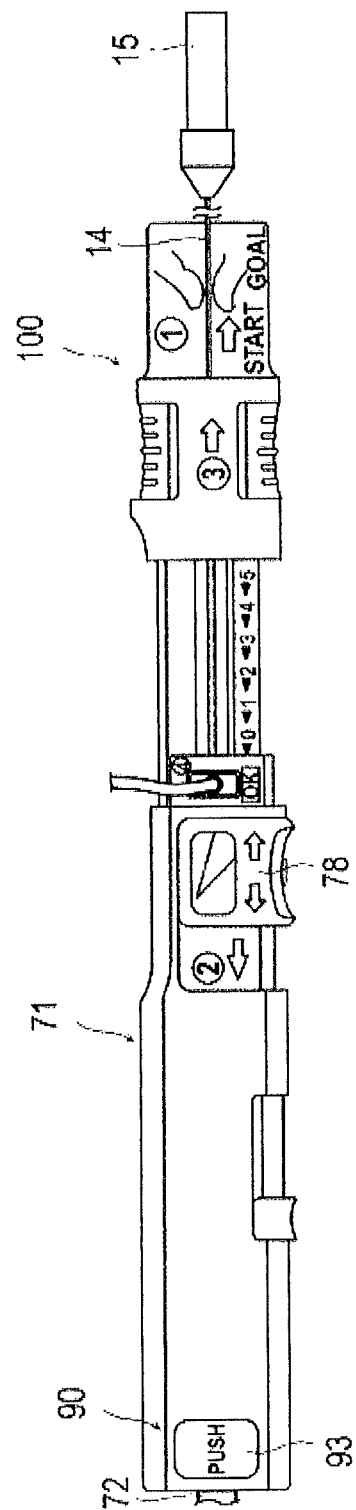

FIG. 17 is a plan view of the operation unit at the operator's side in a state of causing the needle operating lever to retract.

Figure 18:
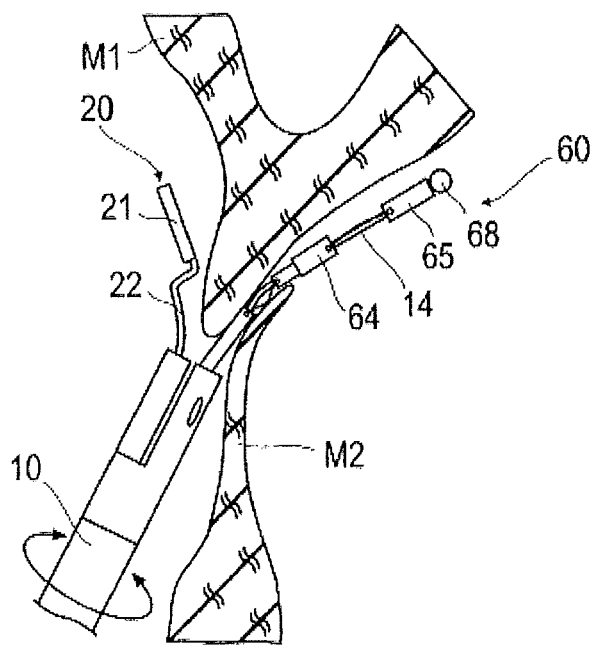

FIG. 18 is a schematic cross-sectional view showing a state where positioning hold means has been inserted into the foramen ovale.

Figure 19:
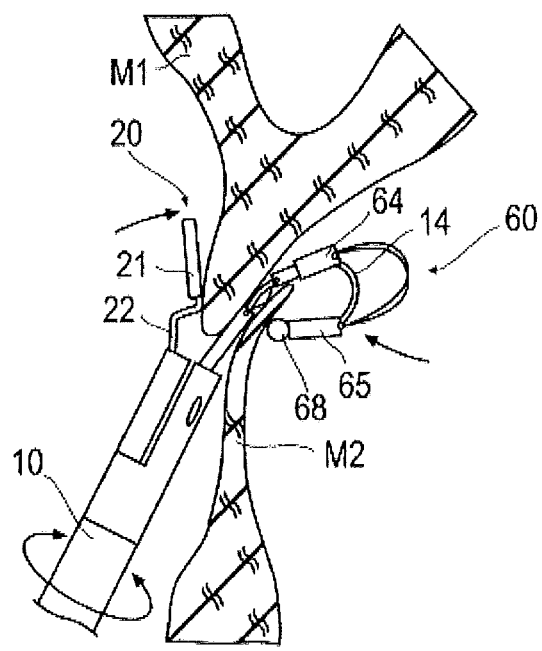

FIG. 19 is a schematic cross-sectional view showing a state where the foramen ovale valve and the atrial septum secundum are being held by the positioning hold means.

Figure 20:
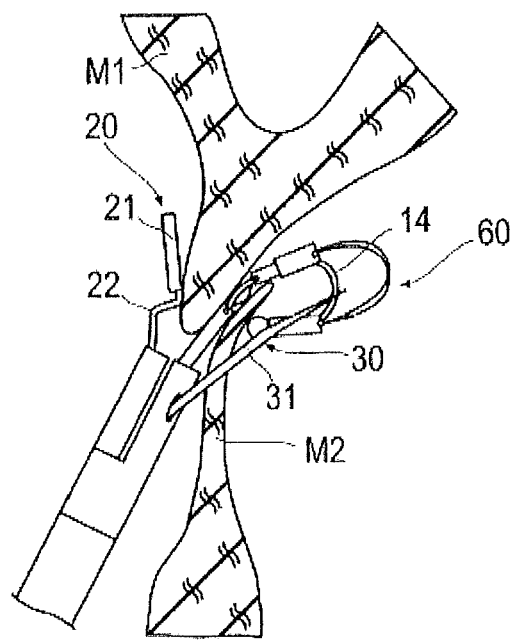

FIG. 20 is a schematic cross-sectional view showing a state where the needle portion has been stuck into the held foramen ovale valve and the atrial septum secundum.

Figure 21:
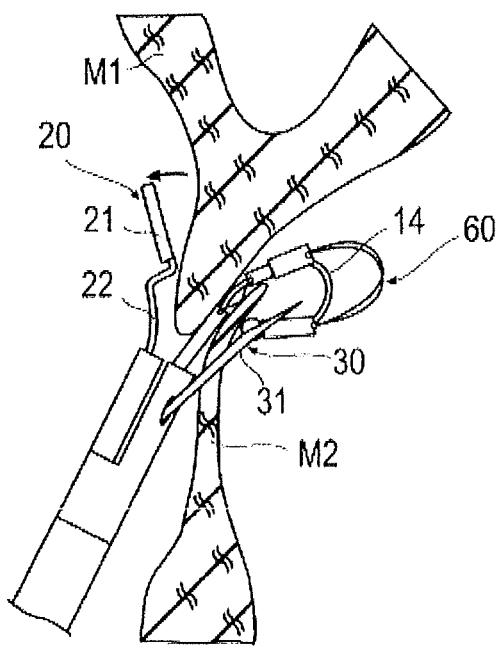

FIG. 21 is a schematic cross-sectional view showing a state where a sandwiching portion has been separated from the atrial septum secundum.

Figure 22:
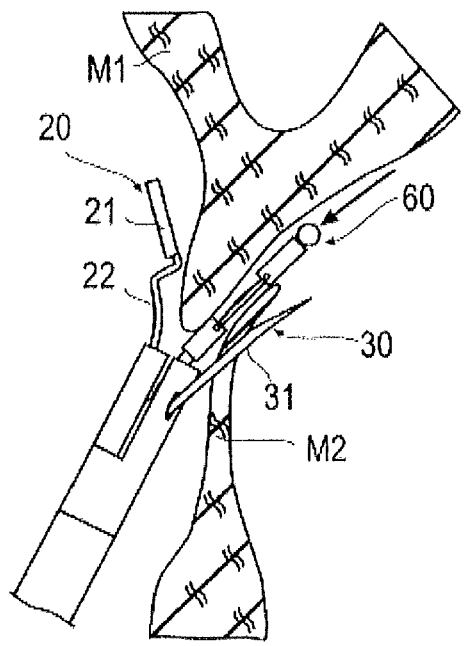

FIG. 22 is a schematic cross-sectional view showing a state where the positioning hold means is accommodated in the device.

Figure 23:
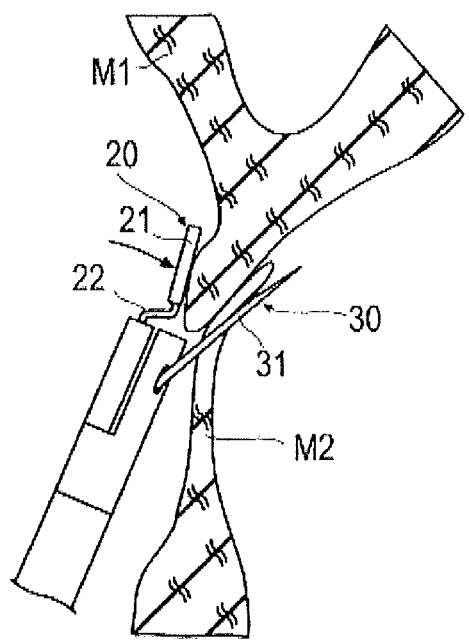

FIG. 23 is a schematic cross-sectional view showing a state where the foramen ovale valve and the atrial septum secundum are sandwiched between the needle portion and the sandwiching portion.

FIGS. 24(A) to 24(D) are schematic views showing the operation state of the positioning hold means.

Figure 25A:
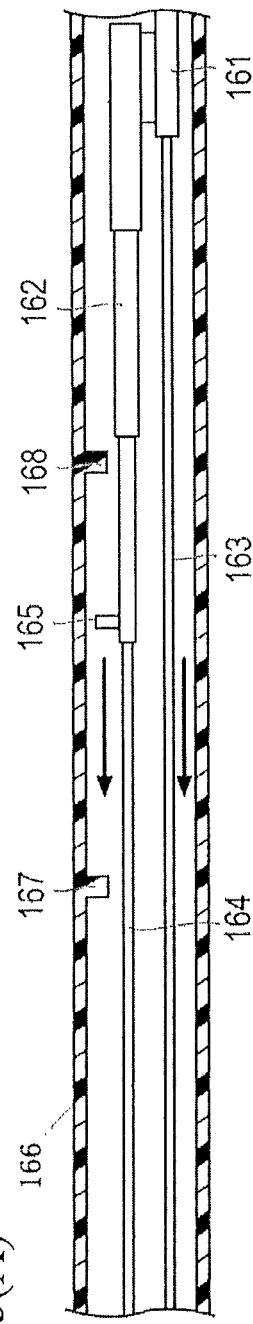
Figure 25B:
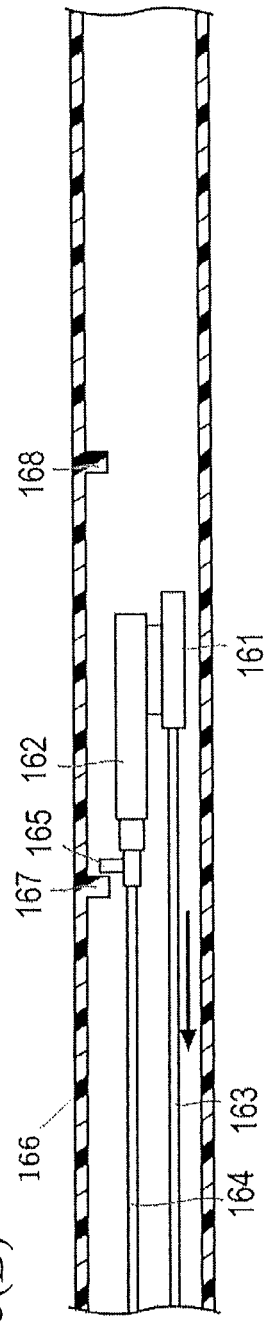

FIGS. 25(A) and (B) are cross-sectional views showing a state where the operation unit is caused to advance in a modification example of the action switching portion, wherein FIG. 25(A) shows a state where an engagement portion has not yet come into contact with a deformation inducing portion positioned ahead of the engagement portion, and FIG. 25(B) shows a state where the engagement portion has come into contact with the deformation inducing portion positioned ahead of the engagement portion.

Figure 26A:
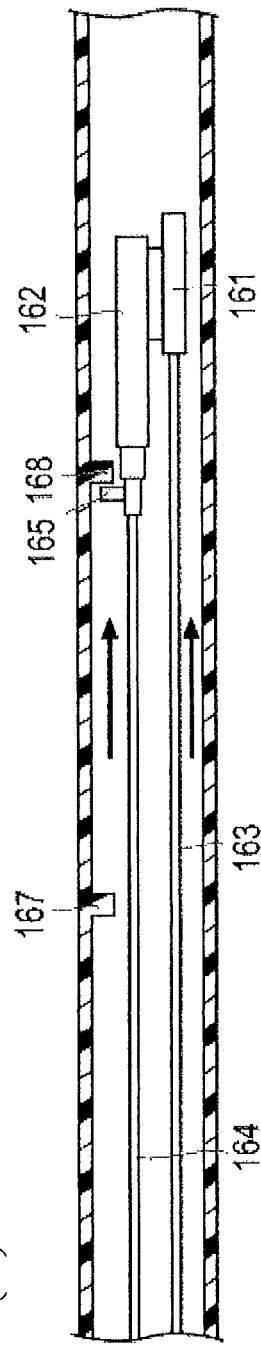
Figure 26B:
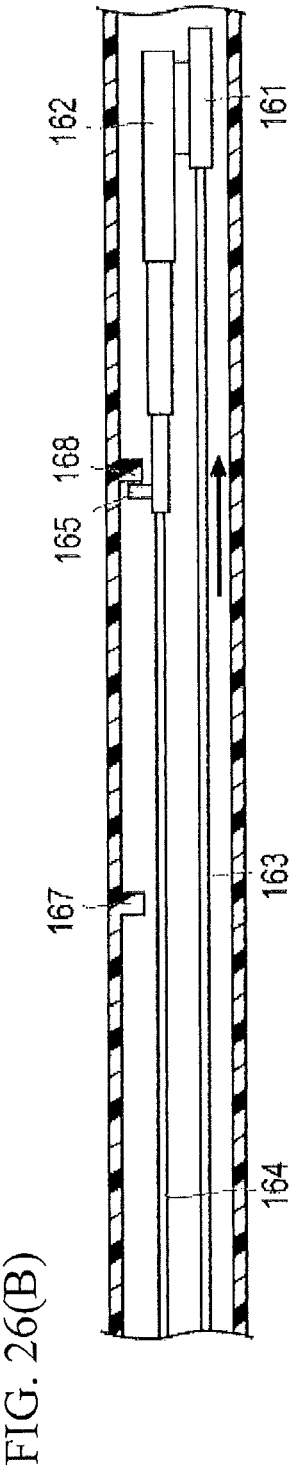

FIGS. 26(A) and (B) are cross-sectional views showing a state where the operation unit is caused to retract in a modified example of the action switching portion, wherein FIG. 26(A) shows a state where the engagement portion comes into contact with the deformation inducing portion positioned behind the engagement portion, and FIG. 26(B) shows a state where the engagement portion has come into contact with the deformation inducing portion positioned behind the engagement portion.

Figure 27A:
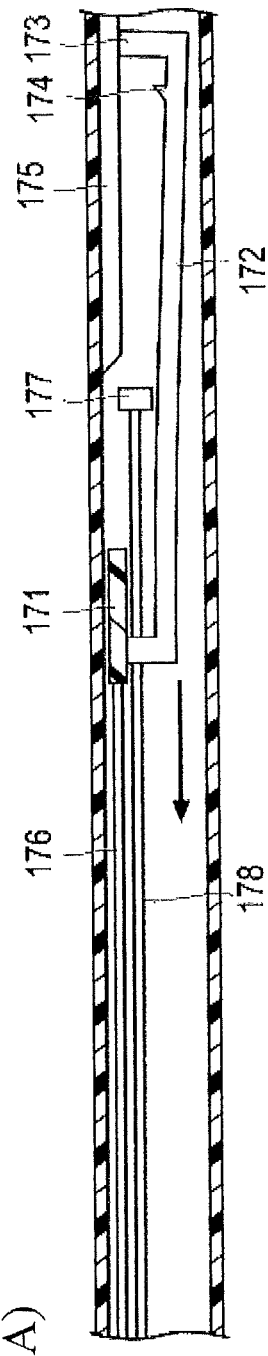
Figure 27B:
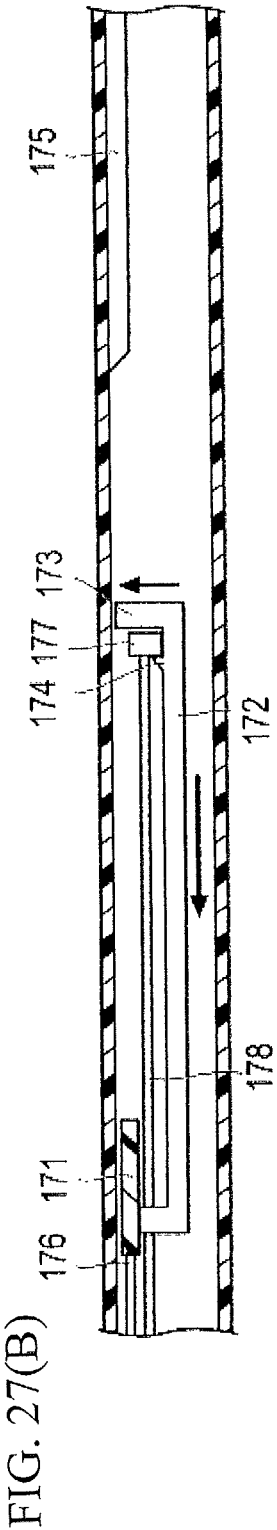
Figure 27C:
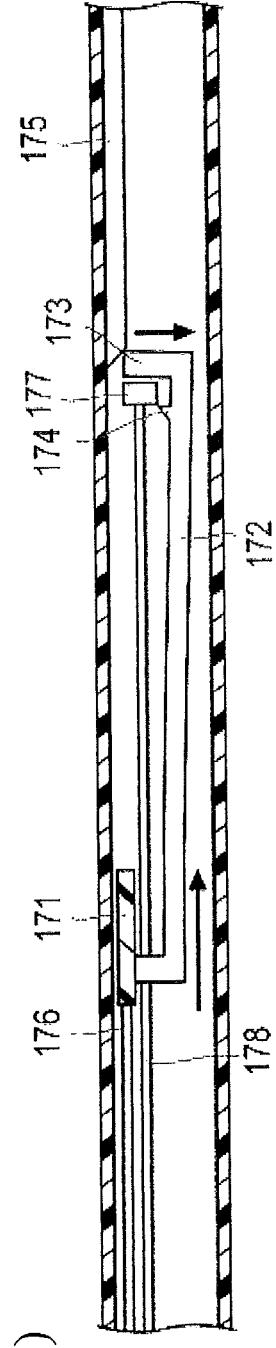

FIGS. 27(A)-(C) are cross-sectional views showing a state where the operation unit is caused to advance and retract in another modification example of the action switching portion, wherein FIG. 27(A) shows a state where the engagement portion has not yet been separated from the deformation inducing portion when the operation unit is advancing, FIG. 27(B) shows a state where the engagement portion moves forward from the deformation inducing portion due to advance of the operation unit, and FIG. 27(C) shows a state where the engagement portion has come into contact with the deformation inducing portion due to retraction of the operation unit.

DETAILED DESCRIPTION

Embodiments of a medical device representing examples of the inventive medical device disclosed here will be described below in detail with reference to the accompanying drawing figures. The dimensional ratio in the drawings is exaggerated and different from the actual ratio for the convenience of description.

The medical device according to the embodiment disclosed here is a PFO closure device. The device will first be described with reference to FIGS. 1 to 5. In FIG. 2, only the operation unit at the operator's side 70 is described in a state of being miniaturized due to space constraints.

Figure 1:
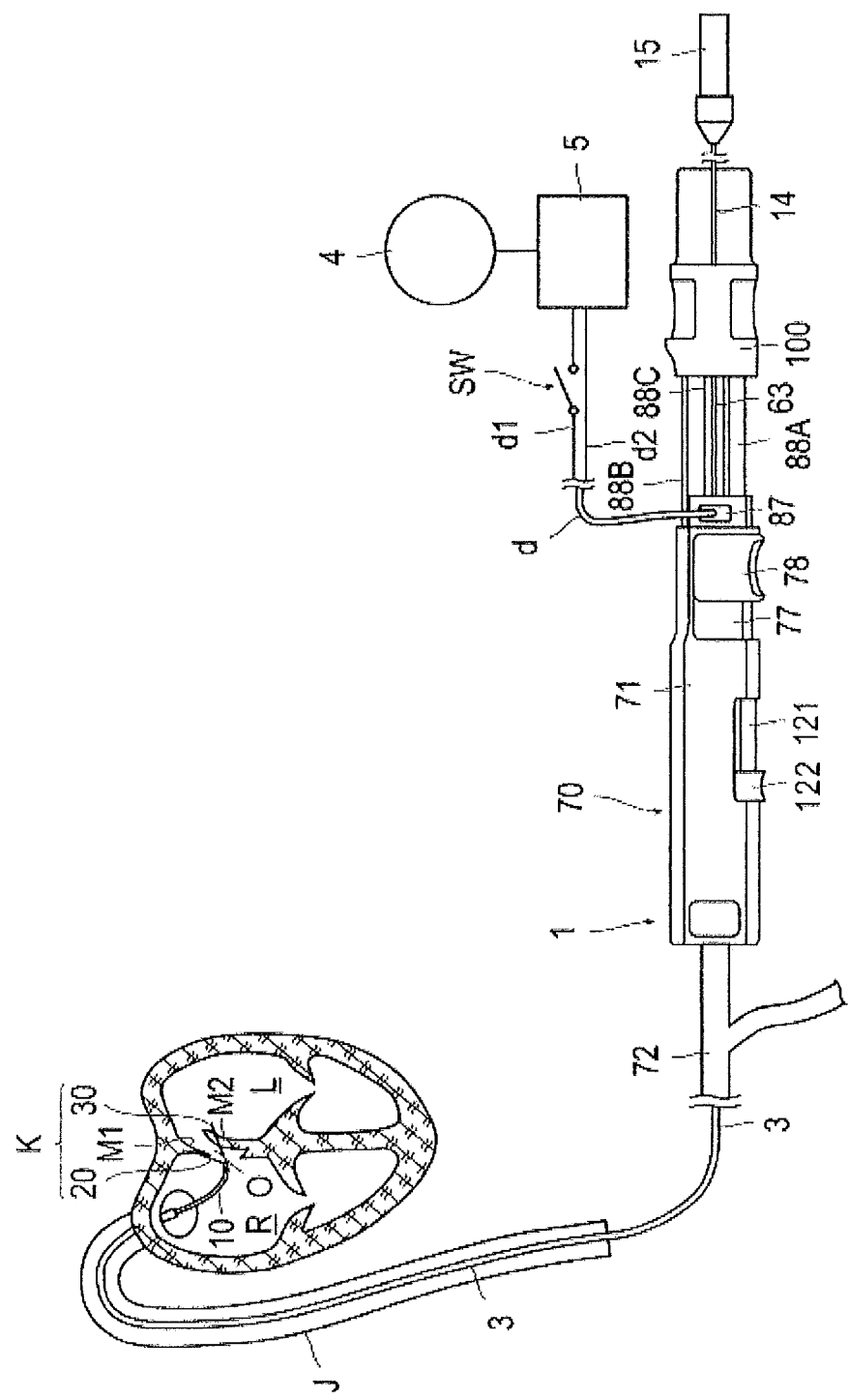
FIG. 1 is a schematic cross-sectional view of a medical device representing an example of the medical device disclosed here.
Figure 2:
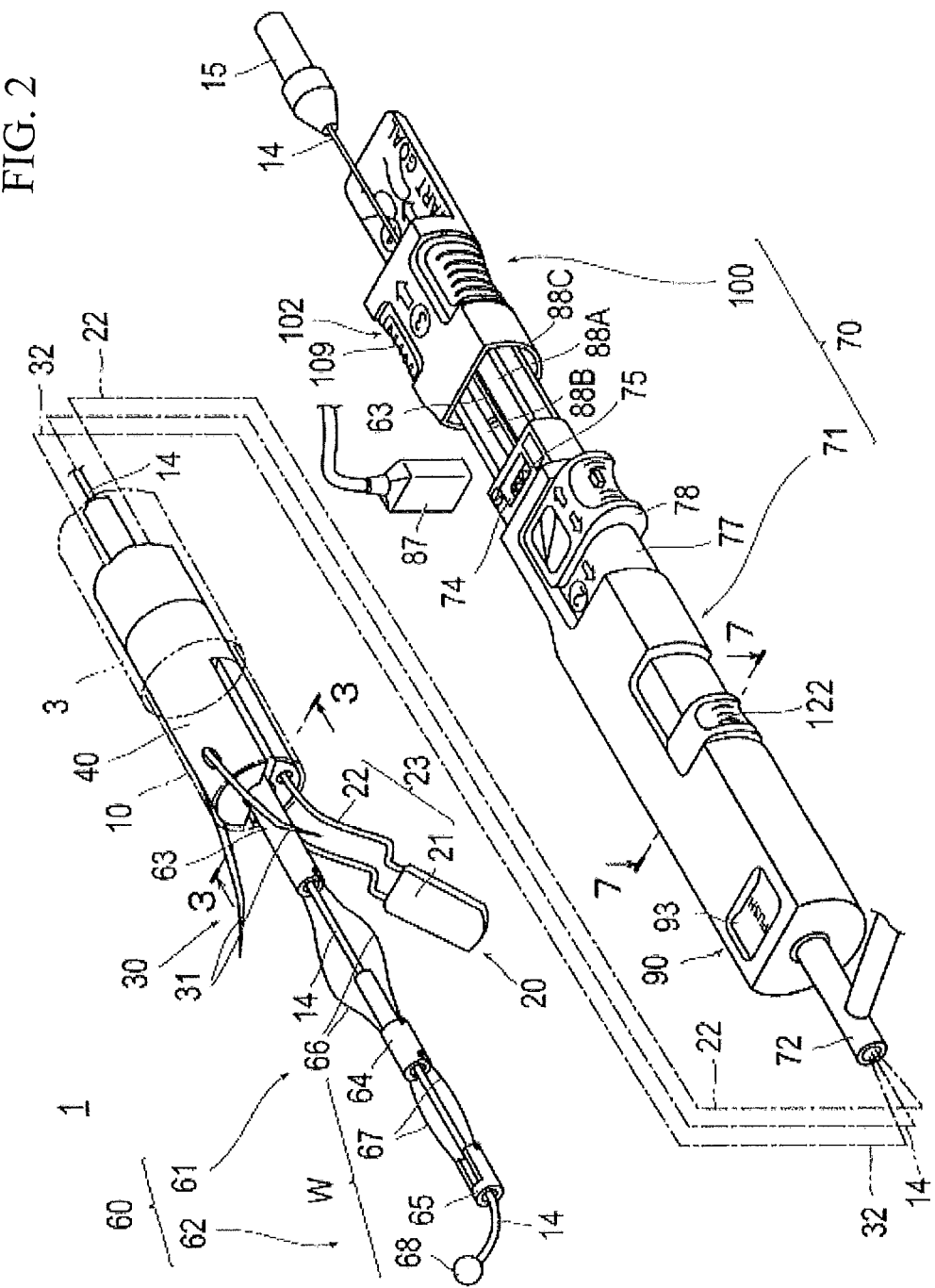
FIG. 2 is a perspective view of main portions of the medical device.

As shown in FIGS. 1 and 2, the PFO closure device includes a catheter 1 (cylindrical body) configured to be inserted into a living body and constituted of a catheter main body 10 and an operation unit at the operator's side 70 which is mounted on the proximal end of the catheter main body 10, a guiding catheter 3 having a proximal end to be interlocked with the operation unit at the operator's side 70 and into which the catheter main body 10 is inserted, and an energy supply or energy supply means 4 that supplies electric energy for causing fusion or necrosis of a biological tissue M (a generic term for biological tissues M1 and M2). The catheter 1 includes a clamp or clamping means K that is disposed in the distal portion of the catheter main body 10 for clamping a foramen ovale valve M2 and an atrial septum secundum M1, and positioning hold means 60 (positioning portion) that holds and positions the biological tissue M so as to cause the procedure performed by the clamping means K to be stably and reliably conducted. In the following description, in the device, the side of the operation unit at the operator's side 70 is called the "proximal end", and the side of the clamping means K is called the "distal end". In addition, the "catheter" refers to an instrument having a tubular body used for medical purposes.

For using the device, first, a guiding catheter 3 is inserted through, for example, a femoral vein J, in a state where the guiding catheter 3 is accommodating both the clamping means K disposed at the distal end of the catheter main body 10 and the catheter main body 10 in the inside thereof. After the distal end reaches a site of the heart subjected to the procedure, the operation unit at the operator's side 70 is operated, such that the clamping means K protrudes from the catheter main body 10 and clamps tissues including the atrial septum secundum M1 of the heart where a defect O as the foramen ovale (hereinafter, simply called a "foramen ovale O" in some cases) is formed and the foramen ovale valve M2. In the state where the tissues are being clamped as above, electric energy is supplied to the clamping means K to cause the fusion of both the tissues by heating, whereby the defect O is closed. That is, the clamping means K functions as a heating portion. In the drawings, "L" indicates the left atrium, and "R" indicates the right atrium.

Figure 3:
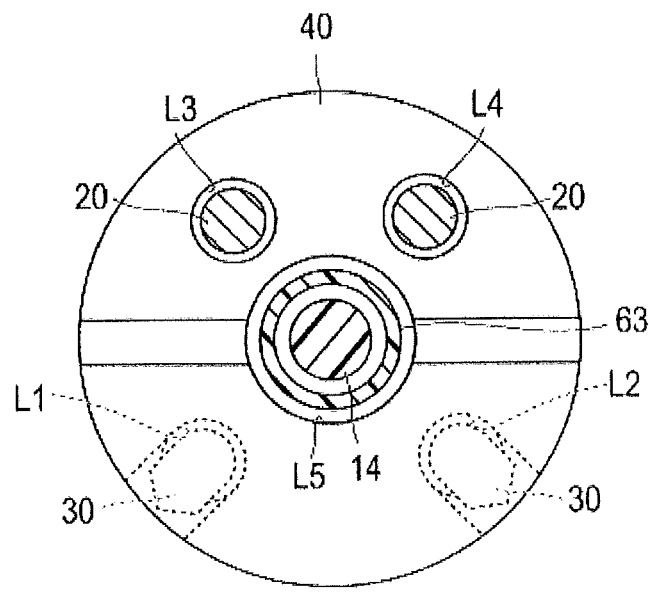
FIG. 3 is a cross-sectional view of the distal portion of a catheter taken along the section line 3-3 in FIG. 2.

In the embodiment shown by way of example, the clamp or clamping means K is constituted by a sandwiching portion 20 that comes into direct contact with one side of the atrial septum secundum M1, and a needle portion 30 that is stuck into the foramen ovale valve M2. The sandwiching portion 20 includes a sandwiching shaft 23 that consists of a flat plate portion 21, which is flat overall, and a pair of wire portions 22 connected to the proximal portion of the flat plate portion 21, and a terminal 83 (proximal member) (see FIG. 7) that is disposed at the proximal side or proximal end of the wire portions 22. As shown in FIG. 3, the plan position of the sandwiching portion 20 is restricted by lumens L3 and L4 of a distal tip 40 that is fixed to the distal end of the catheter main body 10.

Figure 4:
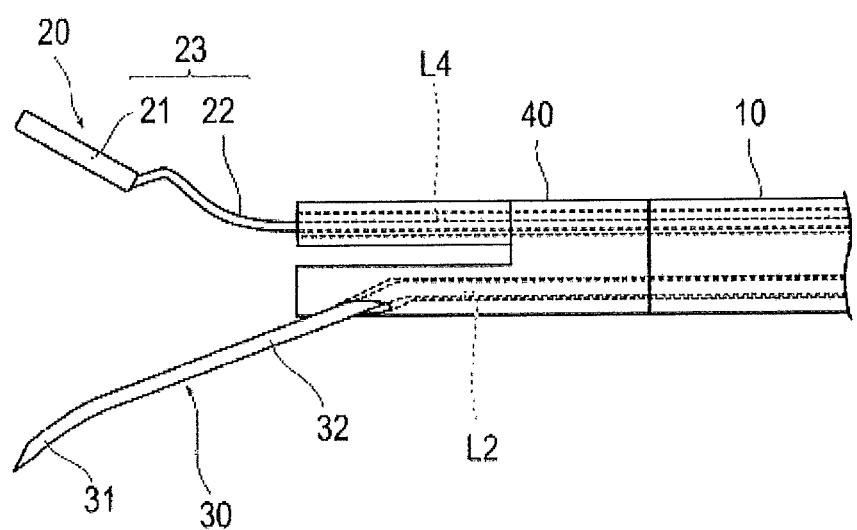
FIG. 4 is a plan view of the distal portion of the catheter in a state where a sandwiching portion and a needle portion protrude from a lumen.
Figure 5:
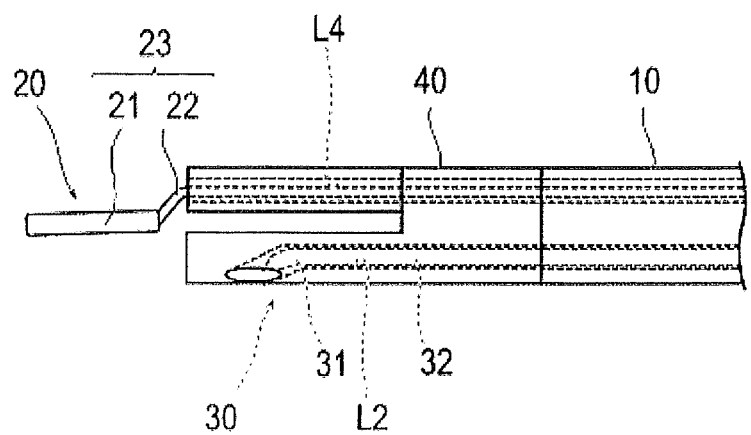
FIG. 5 is a plan view of the distal portion of the catheter in a state where the sandwiching portion and the needle portion are accommodated in the lumen.

The distal side of the wire portions 22 is formed in a state of being curved. That is, the distal side of the wire portions 22 is curved. When the wire portions 22 are pushed into the lumens L3 and L4, the curve of the wire portions 22 is straightened as shown in FIGS. 4 and 5 and is deformed elastically so as to have a shape close to a straight line. As a result, the flat plate portion 21 disposed closer to the distal side than to the wire portions 22 moves toward the needle portion 30.

The needle portion 30 includes two needle distal portions 31 that are held in the distal tip 40, two needle proximal portions 32 that extend from the proximal side of each of the needle distal portions 31 to the operation unit at the operator's side 70, and a terminal 81 (see FIG. 7) that is disposed at the proximal side of the needle proximal portions 32. The terminal 81 at the proximal side of the needle proximal portions 32 is connected to a needle operation lever 78 that is disposed in the operation unit at the operator's side 70 to operate the needle portion 30. Each needle distal portion 31 is integrated with a respective needle proximal portion 32 so that the two portions are formed of a single wire.

The needle distal portions 31 are held so as to be able to advance and retract in the two lumens L1 and L2 (see FIG. 3) formed in the distal tip 40. As shown in FIGS. 4 and 5, when the needle distal portions 31 are caused to advance and retract in the axial direction, the sharp distal portions can appear from or disappear into the distal tip 40. That is, the advancing movement of the needle distal portions 31 causes the needle distal portions 31 to extend distally beyond the distal end of the tip 40, and the retracting movement of the needle distal portions 31 causes the needle distal portions 31 to be positioned inside of and covered by the tip 40.

Both the sandwiching portion 20 and the needle portion 30 function as electrodes for applying electric current to the biological tissue M. The wire portions 22 of the sandwiching portion 20 or the needle portion 30 are inserted into the catheter main body 10, and are electrically connected to the energy supply means 4 through an input connector 75 disposed in the operation unit at the operator's side 70, an output connector 87 (see FIG. 1) that is a plug configured to be fit into the input connector 75, a conductor wire d (a generic term for d1 and d2) connected to an electrode terminal of the output connector 87, and a control unit 5. Either the conductor wire d1 or d2 (the conductor wire d1 in the present embodiment) is provided with a foot switch SW disposed at the side of the operator's foot, so as to control on and off of the electric current from the energy supply means 4. Instead of the foot switch SW, a switch that can be rather easily operated manually may be provided.

The operation unit at the operator's side 70 is a portion for operating the clamping means K, which is a pair of electrode members clamping the biological tissue M in the vicinity of a defect present in a biological tissue, such that the clamping means K freely appears from (extends outwardly beyond) or disappears into the distal end of the catheter main body 10. However, in the operation unit at the operator's side 70, in order that all operations can be performed in a relatively small area without moving a hand too much, the following are collectively provided.

That is, as shown in FIG. 2, the operation unit at the operator's side 70 is provided with the needle operation lever 78 that operates the needle portion 30 as an electrode member at one side, a slide portion 100 (operation unit) that operates the positioning hold means 60, a sandwiching portion operation lever 122 (operation member) that operates the sandwiching portion 20 as an electrode member at the other side, and an operation wire 14 that is for assisting the operation of the clamping means K and is inserted into the operation unit at the operator's side 70 and the catheter main body 10 so as to be movable in the axial direction. Moreover, the operation unit at the operator's side 70 is provided with a grasping member 15 that is interlocked with the proximal portion of the operation wire 14 to operate the operation wire 14, a pusher piece 109 that operates a lock-unlock mechanism 102 (see FIG. 12), which locks or unlocks the sliding movement of the slide portion 100, and locks the axial direction movement of the operation wire 14, and the input connector 75 that includes the electrode terminal connected to the energy supply means 4 supplying heat energy.

A distal member 68 and the grasping member 15 are respectively disposed at the distal end and the proximal end of the operation wire 14.

As shown in FIG. 6, in order that the process performed in various sequences can be visually checked, the operation unit at the operator's side 70 is provided with a process display portion H (a generic term for H1 to H6) of which the surface is marked with various signs for guiding the operator to correctly operate the device (see FIG. 14(B) regarding a process display portion H5).

The operation unit at the operator's side 70 will be described in more detail. As shown in FIG. 2, the operation unit at the operator's side 70 includes a main body portion 71 at the side with which the guiding catheter 3 is interlocked, the slide portion 100 that is interlocked with the proximal side of the main body portion 71 through guide bars 88A, 88B, and 88C so as to approach and be separated from the main body portion 71. On the upper surface of the main body portion 71, the needle operation lever 78 that operates the needle portion 30 and the sandwiching portion operation lever 122 that operates the sandwiching portion 20 are disposed.

Figure 8:
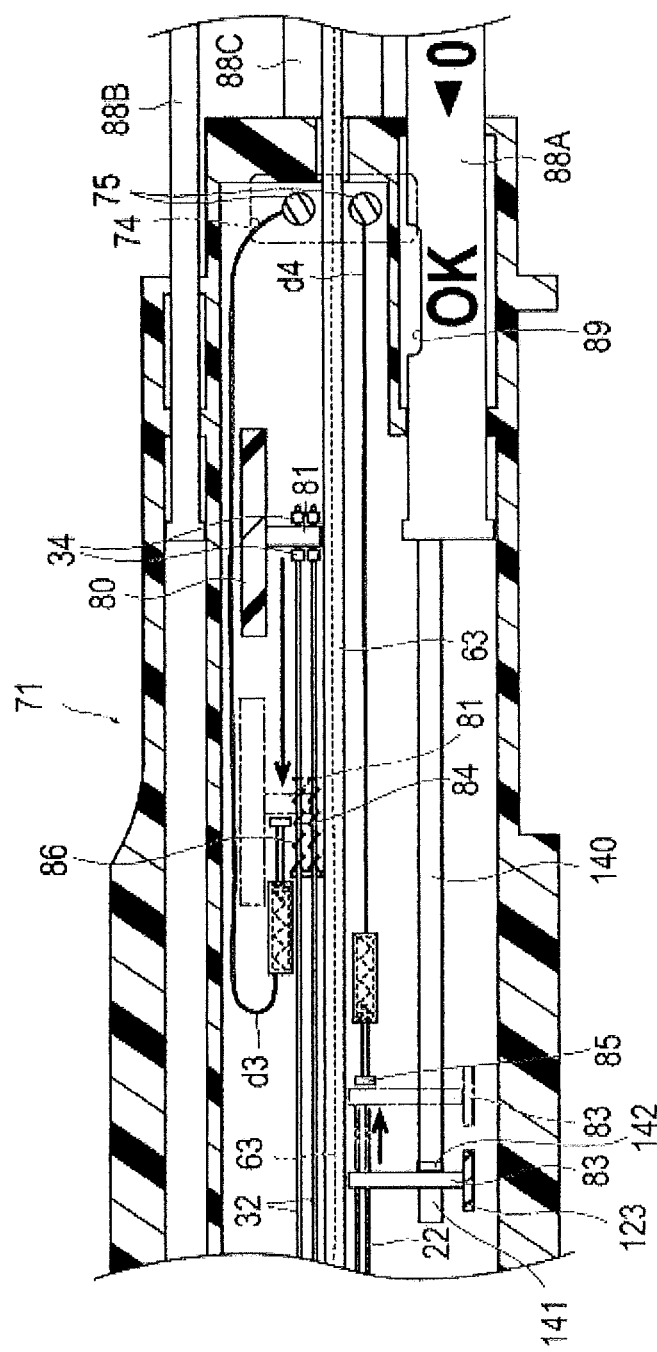
FIG. 8 is an enlarged cross-sectional view of the operation unit at the operator's side taken along the section line 7-7 in FIG. 2.

As shown in FIG. 6, a concavity 77 is formed on the surface (upper surface) of the main body portion 71. The needle operation lever 78 is disposed in the concavity 77 so as to be able to slide in a longitudinal direction (see white arrows). As shown in FIGS. 7 and 8, the needle operation lever 78 includes a bracket 80 that protrudes to reach an internal space 76 by being inserted through a slit formed in the main body portion 71. The bracket 80 is interlocked with a terminal 81 connected to the proximal side of the needle proximal portions 32. Accordingly, when the needle operation lever 78 is caused to slide along the slit, the terminal 81 advances and retracts inside the main body portion 71 as shown in FIG. 8, whereby the needle portion 30 is caused to advance and retract.

In addition, as shown in FIG. 6, a concavity 121 is formed on the surface (upper surface) of the main body portion 71, and the sandwiching portion operation lever 122 is disposed in the concavity 121 so as to be able to slide in a longitudinal direction. As shown in FIGS. 7 and 8, the sandwiching portion operation lever 122 includes a bracket 123 that protrudes or passes through a slit in the main body portion 71 to reach the internal space 76. The bracket 123 is interlocked with a terminal 83 (proximal member) connected to the wire portions 22 of the sandwiching portion 20.

A main tube 63, which will be described later, is inserted through a portion which is approximately the center of the internal space 76 of the main body portion 71. The proximal side of the main tube 63 is interlocked with the slide portion 100 by an adhesive and the like (see FIG. 12), and slides by being guided to the main body portion 71 in response to the sliding of the slide portion 100. In this illustrated embodiment, the main tube 62 and the wire portions 22 constitute shaft portions.

In the position where those terminals 81 and 83 terminate their movement, contact members 84 and 85 functioning as switches are disposed. Needless to say, the electric system of the needle portion 30 is insulated from the electric system of the sandwiching portion 20 so as not to cause conduction.

The contact members 84 and 85 are connected to both the electrodes of the input connector 75 through conductor wires d3 and d4. The contact members 84 and 85 have a structure in which when they come into contact with the terminals 81 and 83, which move along with the movement of the needle portion 30 and the sandwiching portion 20, the contact members 84 and 85 retract while coming into contact with the terminals 81 and 83. That is, the contact members 84 and 85 come into contact with the terminals 81 and 83 within a contact zone of a certain length, and they can come into contact with each other in accordance with individual differences of the living body.

The operation wire 14 is disposed inside the main tube 63 and has a function of assisting the operation of the clamping means K by performing a pulling operation in the axial direction. In the main tube 63, the operation wire 14 can rotate a full 360 degrees on the axis. By virtue of the operation wire 14 being rotatable a full 360 degrees, it is possible to insert the distal end of the operation wire 14 to the vicinity of the foramen ovale O, and to insert the distal end into the foramen ovale O by varying the position of the operation wire 14 by rotating the wire. As a result, even if the shape of the foramen ovale O is deformed in various ways, it is possible to insert the distal end of the device into the foramen ovale O regardless of the shape and condition of the foramen ovale O, and the surgery can be performed rather easily and rapidly.

The guide bars 88A, 88B, and 88C are slidably disposed inside the main body portion 71.

Moreover, as shown in FIG. 9(A), inside the main body portion 71 of the operation unit at the operator's side 70, there is an action switching portion 130 which is joined with the guide bar 88A and can be interlocked with and separated from the terminal 83. The action switching portion 130 advances and retracts along with the guide bar 88A in response to the sliding of the slide portion 100. When interlocked with the terminal 83, the action switching portion 130 can cause the sandwiching portion 20, which is connected to the terminal 83, to advance and retract. When separated from the terminal 83, the action switching portion 130 can cause the sandwiching portion 20 to move independently of the slide portion 100, and can cause the slide portion 100 to move independently of the sandwiching portion.

The action switching portion 130 includes a girder-like interlock member 140 that extends to the distal side from the position where the interlock member 140 is fixed to the guide bar 88A, and a deformation inducing portion 150 that is formed in the main body portion 71 and deforms the interlock member 140 by coming into contact with the interlock member 140. The proximal side (right side in FIG. 9) of the interlock member 140 is fixed to the guide bar 88A, and an engagement portion 141 that can be engaged with or separated from the terminal 83 is formed at the distal side (left side in FIG. 9) thereof. The interlock member 140 is separably interlocked with the terminal 83. The engagement portion 141 includes a first engagement portion 142 that protrudes from the distal portion of the interlock member 140 in a direction orthogonal to the direction of the advance and retraction, and a second engagement portion 143 that is spaced from and disposed closer to the proximal side than to the first engagement portion 142 of the interlock member 140 and protrudes in the same direction as the first engagement portion 142. The first engagement portion 142 is configured to engage or contact the surface of the distal side of the terminal 83, and the second engagement portion 143 is configured to engage or contact the surface of the proximal side of the terminal 83. The terminal 83 is sandwiched between the first engagement portion 142 and the second engagement portion 143. Therefore, when the interlock member 140 is moved to the distal side or in the distal direction in a state where the terminal 83 is sandwiched between the first engagement portion 142 and the second engagement portion 143, the terminal 83 is also pushed and moved to the distal side due to the second engagement portion 143. Inversely, when the interlock member 140 is moved to the proximal side, the terminal 83 is also pushed and moved to the proximal side due to the first engagement portion 142 (see FIG. 10(B)). The surface of the proximal side of the second engagement portion 143 forms a slope 144 of which the apex forms a relatively sharp angle.

The deformation inducing portion 150 is disposed at the distal side of the interlock member 140. The surface of the proximal side of the deformation inducing portion 150 forms a taper surface 151 that slants or is angled with respect to the direction of the advancing and retracting movement of the interlock member 140. As shown in FIG. 9(B), when the interlock member 140 moves to the distal side, the taper surface 151 comes into contact with the end of the protrusion direction of the first engagement portion 142, and deforms the distal end of the interlock member 140 such that the interlock member 140 is bent toward a direction opposite to the direction in which the first and second engagement portions 142 and 143 protrude. When the interlock member 140 is deformed, the terminal 83 escapes from the position between the first and second engagement portions 142 and 143, whereby the interlock member 140 is disengaged from the terminal 83. As a result, as shown in FIG. 9(C), even if the interlock member 140 is further moved to the distal side, it is possible to move the sandwiching portion 20 independently of the slide portion 100 without moving the terminal 83 to the distal side.

When the interlock member 140, which has been moved toward the distal end, is pulled back to the proximal side, and the first engagement portion 142 is moved closer to the proximal side than to the deformation inducing portion 150, the interlock member 140 having been bent recovers its original shape as shown in FIGS. 10(A) and (B). Moreover, since the slope 144 is formed at the proximal side of the second engagement portion 143, the second engagement portion 143 smoothly goes over or moves past the terminal 83 and moves to the proximal side of the terminal 83, whereby the terminal 83 is sandwiched or held again between the first and second engagement portions 142 and 143. Furthermore, when the interlock member 140 is moved to the proximal side, the terminal 83 is also pulled and moved to the proximal side due to the first engagement portion 142, whereby the sandwiching portion 20 retracts as shown in FIG. 10(C). In this manner, the action switching portion 130 can cause the sandwiching portion 20 to move along with or separately from the slide portion 100 according to the advance and retraction of the slide portion 100.

The distal portion of the main body portion 71 is provided with a push button 93 of an interlock mechanism 90 (see FIG. 2). The interlock mechanism 90 is for causing a Y-connector 72 to be easily detached from and attached to the main body portion 71. A flange portion may be disposed in the proximal portion of the Y-connector 72, and this flange portion can be fitted to an insertion hole formed in the main body portion 71 while the push button 93 is being pushed. When the push button 93 is thereafter released from the pushed state, the flange portion of the Y-connector 72 is engaged with an engagement hole 94 of a slide member 91 as shown in FIG. 11. In addition, the slide member 91 has resilience due to the spring member 92 and functions as a stopper of the flange portion. Moreover, the Y-connector 72 can be attached or detached by pushing the push button 93.

As shown in FIG. 2, it is preferable for the distal end of the operation unit at the operator's side 70 to be interlocked with the Y-connector 72, into which contrast media and the like can be injected, through the interlock mechanism 90. However, when the Y-connector 72 is not used, the main body portion 71 can be directly interlocked with the guiding catheter 3 having a flange portion.

The proximal portion of the main body portion 71 is provided with a connection hole 74 matching the exterior shape of the output connector 87. In the inside of the connection hole 74, an electrode terminal of the input connector 75 is disposed (see FIG. 8).

The guide bar 88A is disposed such that a portion of the side of the guide bar 88A enters or crosses the connection hole 74. The guide bar 88A having entered or being located in the connection hole 74 hinders the output connector 87 from being inserted into the connection hole 74 so as to prevent the connection between the output connector 87 and the input connector 75. A cutout portion 89 is formed in a portion of the side of the guide bar 88A. When the slide portion 100, the guide bar 88A, and the main tube 63 retract together from the main body portion 71, and the cutout portion 89 matches with the connection hole 74, the output connector 87 can be connected to the input connector 75. In this manner, the connection between the energy supply means 4 and the input connector 75 that is the most important procedure during the surgery and needs to be conducted very carefully is not performed until the biological tissue M is completely sandwiched, hence safety of the procedure is improved.

In addition, as shown in FIG. 6, the main body portion 71 is provided with a window 73 that is opened in a position adjacent to the input connector 75. Moreover, in the guide bar 88A, an "OK" display portion H6 is placed near the cutout portion 89.

When the slide portion 100 is caused to retract from the main body portion 71 such that the positioning hold means 60 is taken back by being pushed into the catheter main body 10, and the terminal 83 which makes the sandwiching portion 20 conductive comes into contact with the contact member 85, the "OK" display portion H6 is finally displayed on the window 73.

The lock-unlock mechanism 102 shown in FIGS. 12 and 13 is disposed in the slide portion 100. When the pusher piece 109 is pushed, the lock-unlock mechanism 102 locks or unlocks sliding of the slide portion 100 and the movement of the operation wire 14 in the axial direction.

The lock-unlock mechanism 102 concurrently uses a first lock portion R1 for the slide portion that interlocks the slide portion 100 with the main body portion 71 by causing an operation member 104 to slide or releases the lock to enable sliding, and a second lock portion R2 for the operation wire that temporarily pauses the advance and retraction of the operation wire 14 in the axial direction when the positioning hold means 60, which will be described later, disposed in the distal portion of the operation wire 14 holds or positions the biological tissue M.

The first lock portion R1 is constituted by the operation member 104 that is freely slidably disposed in a slide hole 103, which is formed in the slide portion 100, and a restriction rod 110 that is integrally provided with the operation member 104 and restricts the movement of the slide portion 100 with respect to the main body portion 71. As illustrated in FIGS. 12 and 13, a spring 107 acts on the operation member 104.

An engagement projection 111a engaging with an engagement recess 111b of the main body portion 71 is disposed at the distal end of the restriction rod 110. Therefore, when the operation member 104 is pushed, the engagement projection 111a disengages from the engagement recess 111b, whereby the slide portion 100 can slide on the main body portion 71. The operation member 104 also includes the second lock portion R2. When the operation member 104 is pushed, the second lock portion R2 is also released.

If the pusher piece 109 and the operation member 104 are operated as described above, release of the first lock portion R1 occurs in tandem with release of the second lock portion R2. Accordingly, the operation of pulling the long operation wire 14 out of the left atrial side can be performed in tandem with the operation of straightening the operation wire 14 for pulling out the operation wire 14. Consequently, it is possible to forestall the pulling operation by which the operation wire 14 that may damage the biological tissue M in a state of being bent is pulled, and to forestall damage or rupture of the biological tissue M.

Meanwhile, the second lock portion R2 for the operation wire 14 is constituted with a locking portion 105 that is formed in the operation member 104 and a larger diameter portion 106 that is fixed to the operation wire 14 and is larger than the outer diameter of the operation wire 14. As materials of the large diameter portion 106, for example, a stainless steel pipe and the like can be used. The large diameter portion 106 is fixed to the operation wire 14 by known techniques such as welding, adhesion, fusion, and the like according to the material. In the second lock portion R2, in order that the advance and retraction of the operation wire 14 in the axial direction is paused temporarily, the locking portion 105 disposed in the operation member 104 is in the form of a wedge-like through hole having a relatively wide-width portion G1 and a relatively narrow-width portion G2. If the locking portion 105 is in the form of the wedge-like through hole as described above, the operation wire 14 is more tightly clamped by the large diameter portion 106 simply by moving through the through hole.

During the procedure, the biological tissue M is held or positioned by the positioning hold means 60, and then a sticking operation using the needle portion 30 is conducted. However, the biological tissue M is held or positioned by pulling the operation wire 14. Even if the biological tissue M is held or positioned by pulling the operation wire 14, the sticking operation cannot be performed unless the tissue is kept in the state of being held or positioned. Accordingly, when the pulling operation of the operation wire 14 is performed, the second lock portion R2 causes the large diameter portion 106 to be locked in the locking portion 105 (a rim portion 105a of the through hole in some cases) such that the operation wire 14 is temporarily locked. Therefore, even when the operator loses his/her hold of the operation wire 14, the tissue can be kept in the state of being held or positioned as described above, and only the sticking operation using the needle portion 30 can be performed independently.

Moreover, when the lock is released, due to the elasticity of elastic wires 66 and 67 in a hold portion 62, the distal portion of the operation wire 14 is automatically straightened, hence the foramen ovale valve M2 can be simply released from the state of being held.

In the internal path of the slide portion 100 into which the operation wire 14 is inserted, a movement restriction-hole 108 having a size that makes it impossible for the large diameter portion 106 to pass toward the proximal end is formed. Therefore, when pulled, the operation wire 14 can be pulled until the large diameter portion 106 fixed to the operation wire 14 reaches the movement restriction-hole 108, but after that, the operation wire 14 cannot be moved in the slide portion 100 any further.

The energy supply means 4 shown in FIG. 1 is for supplying electric energy to the clamping means K and is constituted of a known system. Therefore, details of the energy supply means 4 will not be described. However, from the viewpoint of ease of control, it is preferable for the energy supply means 4 to be electric, either a DC power source or an AC power source. Here, the energy supply means 4 is not limited to the above, and any source may be used as long as it can supply energy which makes it possible to melt the foramen ovale valve M2 and the atrial septum secundum M1 clamped by the clamping means K and to tightly bond M2 to M1 by using an adhesive factor such as collagen or elastin. For example, it is possible to use ultrasound, laser, microwaves, high-frequency waves or the like.

As shown in FIG. 2, the positioning hold means 60 is roughly constituted by a needle positioning portion 61 that positions the needle portion 30 for the foramen ovale O, a hold portion 62 that non-retractably holds the foramen ovale valve M2 such that the foramen ovale valve M2 cannot retract in the sticking direction of the needle portion 30, and the main tube which is an elongated tube 63 that is fixed to and held by the slide portion 100. Ordinarily, the positioning hold means 60 is accommodated in the guiding catheter 3. However, when used, the positioning hold means 60 is pushed out of the guiding catheter 3 by the operation of the operation wire 14 and the main tube 63 as shown in the drawing.

To be more specific, the central lumen L5 formed in the distal tip 40 is provided with the main tube 63 and the operation wire 14 which is provided so as to freely advance and retract in the axial direction inside the main tube 63 (see FIG. 3). The proximal side of the main tube 63 is fixed to and held by the slide portion 100. The main tube 63 functions as a central axle of the medical device. The main tube 63 also reinforces the catheter main body 10 and takes back the positioning hold means 60 by pulling it into the catheter main body 10. The operation wire 14 starts from the distal end of the catheter main body 10, passes through the inside of the main tube 63 and the internal path of the slide portion 100, and protrudes out of the rear end. The proximal portion of the operation wire 14 is interlocked with the grasping member 15 that the operator grasps with his/her fingers to cause the operation wire 14 to advance, retract, or rotate.

The distal portion of the main tube 63 is provided with the needle positioning portion 61. The needle positioning portion 61 positions the needle portion 30 for the foramen ovale O. As shown in FIG. 2, the needle positioning portion 61 is constituted with a pair of first elastic wires 66 that expand or contract by the operation of the operation wire 14. The proximal end of the first elastic wires 66 is mounted on the outer surface of the main tube 63, and the distal end of the first elastic wires 66 is mounted on the proximal side of an intermediate sleeve 64 into which the operation wire 14 is inserted.

When the operation wire 14 is operated to advance and retract in the axial direction, the needle positioning portion 61 causes the first elastic wires 66 to expand to the outside by using the proximal end mounted on the main tube 63 as a supporting point. As a result, each of the first elastic wires 66 pushes the inner circumference of the foramen ovale O with the approximately same degree of elastic force, and the needle portion 30 is aligned with respect to the foramen ovale O. That is, the needle positioning portion 61 performs a function of positioning the needle portion 30, which is between both the first elastic wires 66, in the central portion of the foramen ovale O.

Meanwhile, the hold portion 62 holds the foramen ovale valve M2 from the rear side of the M2 such that the needle portion 30 is rather easily stuck into the foramen ovale valve M2. As shown in FIG. 2, the hold portion 62 includes the distal member 68 that is disposed at the distal portion of the operation wire 14, a distal end sleeve 65, and a pair of second elastic wires 67 that interlock the intermediate sleeve 64 with the distal end sleeve 65. The distal member 68 is fixed to the distal end of the operation wire 14, and the operation wire 14 is inserted into the distal end sleeve 65 and the intermediate sleeve 64. The proximal end of the second elastic wires 67 is fixed to the distal end of the intermediate sleeve 64, and the distal side of the second elastic wires 67 is fixed to the distal end sleeve 65.

The intermediate sleeve 64, the distal end sleeve 65, the second elastic wires 67 that interlocks both the sleeves 64 and 65 with each other, and the distal member 68 constitute a curving mechanism W that bends or curves the distal portion of the operation wire 14.

The curving mechanism W is used for holding the foramen ovale valve M2. When the needle portion 30 is stuck into the foramen ovale valve M2, if the thin foramen ovale valve M2 is held from the rear side thereof, sticking can be easily performing. Therefore, when the operation wire 14 is caused to retract in the axial direction, the curving mechanism W bends or curves the second elastic wires 67 between the distal member 68 and the distal side of the first elastic wires 66 so as to hold the foramen ovale valve M2 from the rear side of the M2 by using the distal member 68 and the distal end sleeve 65. That is, the curving mechanism W causes the distal portion of the operation wire 14 to be bent or curved by using the distal side of the first elastic wires 66 mounted on the main tube 63 as a supporting point.

Here, the curving mechanism W of the hold portion 62 needs to be configured such that this mechanism is curved and holds the foramen ovale valve M2 after the first elastic wires 66 of the needle positioning portion 61 aligns and positions the needle portion 30 with respect to the foramen ovale O. Consequently, the first elastic wires 66 need to be deformed before the second elastic wires 67 are deformed. Therefore, in the present embodiment, the elastic members or wires 66 differ in terms of rigidity relative to the elastic members or wires 67.

When the slide portion 100 is caused to advance and retract in the main body portion 71, the main tube 63 fixed to the slide portion 100 can be pulled into the central lumen L5 of the catheter main body 10, and accordingly, the entire positioning hold means 60 can be taken back into the catheter main body 10.

Next, the action of the present embodiment will be described.

(1) Pre-Process

The operator inserts an introducer (an assembly consisting of a dilator inserted in a long sheath) into the femoral vein J. The distal end of the long sheath is passed through the right atrium R and sent to the left atrium L, and then the dilator is removed from the long sheath.

Then the pusher piece 109 of the first lock portion R1 in the lock-unlock mechanism 102 is pushed toward the inside of the slide portion 100, such that the operation member 104 moves into the slide hole 103, and the restriction imposed by the restriction rod 110 is removed. As a result, the slide portion 100 is put in a state of being able to move in the main body portion 71. A portion of the side of the guide bar 88A is positioned in or covers a part of the connection hole 74 to hinder the output connector 87 from being connected to the input connector 75. In this manner, accidental power supply from the energy supply means 4 is reliably prevented, and safety is secured.

When the slide portion 100 is caused to retract in the main body portion 71, and the needle operation lever 78 as well as the sandwiching portion operation lever 122 are also caused to retract, the wire portions 22 of the sandwiching portion 20, the needle portion 30, or the like are accommodated in the catheter main body 10. At this time, the interlock member 140 of the action switching portion 130 moves to the proximal side together with the slide portion 100, and the terminal 83 is pulled or moved toward the proximal side due to the first engagement portion 142, whereby the sandwiching portion 20 retracts.

In this state, a catheter is inserted into the long sheath, passes through the femoral vein J and the right atrium R, and sent to the left atrium L.

When the distal end of the catheter main body 10 reaches the left atrium L, the slide portion 100 is caused to advance in the main body portion 71. As a result, the main tube 63 moves forward, and the pusher piece 109 of the lock-unlock mechanism 102 is pushed, whereby a state where the large diameter portion 106 of the operation wire 14 does not touch the narrow-width portion G2 of the through hole 105 formed in the operation member 104 is created. That is, a state where the second lock portion R2 is unlocked to free the operation wire 14.

Thereafter, when the slide portion 100 is caused to advance in the main body portion 71, the positioning hold means 60 advances due to the main tube 63 fixed to the slide portion 100, and the sandwiching portion 20 also advances. That is, as shown in FIG. 9(A), when the slide portion 100 is caused to advance in the main body portion 71, the action switching portion 130 interlocked with the guide bar 88A (interlocked state) fixed to the slide portion 100 advances, and the terminal 83 sandwiched between the first engagement portion 142 and the second engagement portion 143 moves by being pushed toward the distal side by the second engagement portion 143. In this manner, simply by moving the slide portion 100, both the positioning hold means 60 and the sandwiching portion 20 can be moved simultaneously.

When the slide portion 100 is caused to advance by a predetermined length, as shown in FIG. 9(B), the distal end of the interlock member 140 comes into contact with the taper surface 151 of the deformation inducing portion 150, and the interlock member 140 is deformed so as to bend toward the direction opposite to the direction in which the first engagement portion 142 and the second engagement portion 143 protrude. When the interlock member 140 is deformed, the terminal 83 escapes from the position between the first engagement portion 142 and the second engagement portion 143, and the action switching portion 130 is disengaged from the terminal 83 (separate state). As a result, even if the slide portion 100 is further moved to the distal side, the terminal 83 does not move to the distal side, and the sandwiching portion 20 moves independently of the interlock member 140. Subsequently, when the slide portion 100 is further moved to the distal side, the positioning hold means 60 including the main tube 63 advances. Thus, by virtue of the engagement between the interlock member 140 and the terminal 83, the slide unit 100 is operatively connected to both the sandwiching portion 20 and the elongated tube 63 so that axial movement of the slide unit 100 results in axial movement of both the sandwiching portion 22 and the elongated tube 63 together with the slide unit 100. When the interlock member 140 contacts or engages the deformation inducing portion 150, the slide unit 100 is operatively disconnected from the sandwiching portion 20, but the operative connection between the slide unit 100 and the elongated tube 63 is maintained. Thereafter, further axially moving the slide unit 100 after operatively disconnecting the sandwiching portion 20 from the slide unit 100 results in further axial movement of the elongated tube 63 without axially moving the sandwiching portion 20.

Thereafter, from the distal end of the main tube 63, the distal end of the operation wire 14 is caused to protrude out of the distal end sleeve 65. Since a radiopaque marker is placed in the distal member 68, the state of protrusion can be visually checked externally. The operation wire 14 can rotate a full 360 degrees. Therefore, it is possible to cause the operation wire 14 to advance while rotating the wire and to relatively easily insert the wire into the left atrium L.

In the state where the operation wire 14 is being inserted into the left atrium L, as shown in FIG. 18, the operation unit at the operator's side 70 is pulled until the opening portions of the lumens L1 to L5 reach the right atrium R. At this time, the distal end of the operation wire 14 protrudes from the distal end sleeve 65 and is positioned inside the left atrium L. Since the wire portions 22 are in a state of protruding from the lumens L3 and L4, the flat plate portion 21 is separated from the atrial septum secundum M1.

(2) Pulling Process of Operation Wire

Figure 24A:
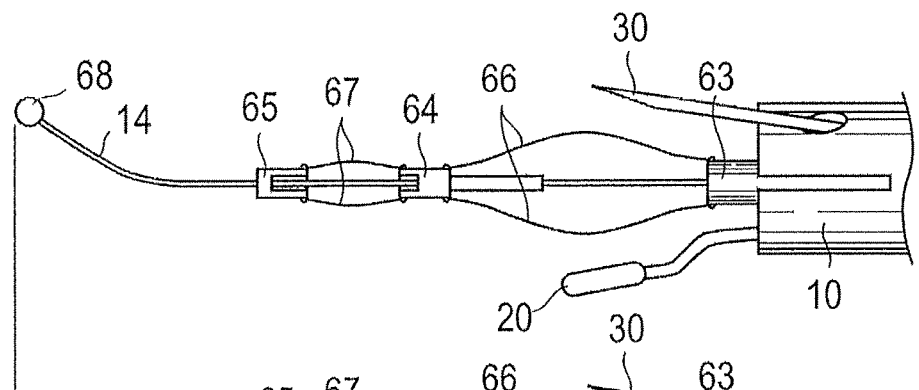
Figure 24B:
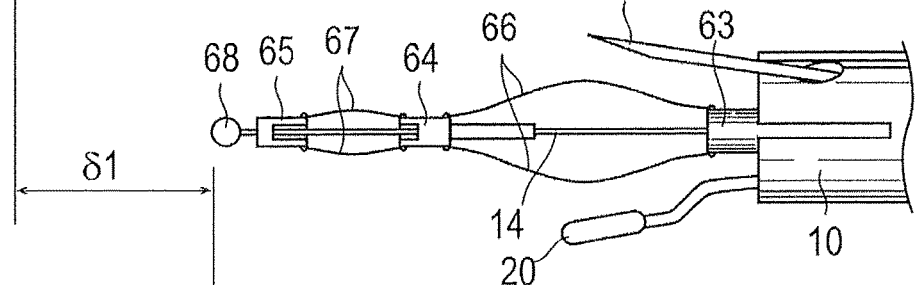

During the pulling process, the operator checks the position of the distal end of the operation wire 14, and then as shown in FIG. 24(B), the operator pulls the grasping member 15 until the distal member 68 at the distal end of the operation wire 14 is attached to or contacts the distal end sleeve 65 such that the operation wire 14 retracts (the wire retracts by a distance "δ1" in FIG. 24B).

When the operation wire 14 is caused to retract, the large diameter portion 106 also retracts. However, in the lock-unlock mechanism 102, as long as the pusher piece 109 is not pushed, the operation member 104 is biased upward due to the resilience of a spring 107, hence the operation wire 14 is always held and sandwiched between the narrow-width portion G2 of the wedge-like through hole 105 and inner circumferential surface of an internal path Qb. Accordingly, during the retraction of the operation wire 14, the wire can be smoothly pulled. Thereafter, the main body portion 71 is operated such that the second elastic wires 67, the sandwiching portion 20, and the needle portion 30 are positioned near the foramen ovale valve M2, whereby the entire hold portion 62 is inserted into the left atrium L side.

Figure 24C:
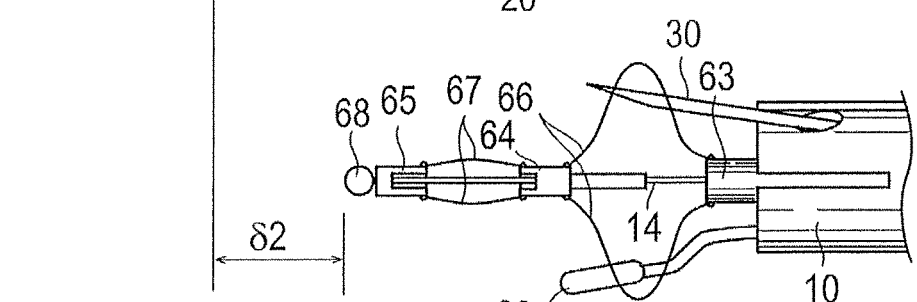

When the operation wire 14 is caused to further retract (the wire retracts by a distance "δ2" of FIG. 24C), the force causing the retraction operation is transmitted from the operation wire 14 to the first elastic wires 66 of which the proximal end is mounted on the main tube 63, through the distal member 68, the distal end sleeve 65, the second elastic wires 67, and the intermediate sleeve 64. As a result, as shown in FIG. 24(C), the first elastic wires 66 protrude toward the outside of the radial direction and are deformed into an arc-like shape. Here, at this point in time, the second elastic wires 67 are not deformed.

As a result, the first elastic wires 66 are deformed while pushing and widening the rim portion of the foramen ovale O. Therefore, the needle portion 30 which is just beside the first elastic wires 66 is aligned with respect to the foramen ovale O and the needle portion 30 is positioned in the center of the foramen ovale O.

Figure 24D:
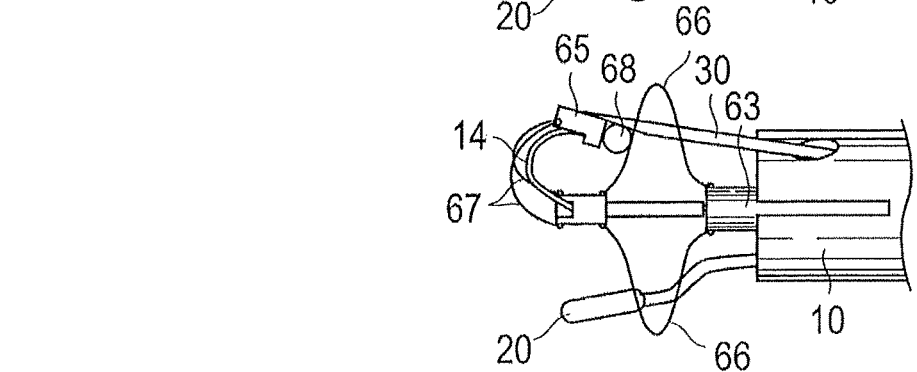

When the operation wire 14 is operated to retract further, and the rear end of the intermediate sleeve 64 is attached to or contacts the distal end of the main tube 63 as shown in FIG. 24(D), while the first elastic wires 66 are not deformed that much, the second elastic wires 67 protrude toward the outside in the radial direction and are deformed into an arc-like shape due to the force of operation. Consequently, as shown in FIG. 19, in the left atrium L, the distal member 68 and the distal end sleeve 65 curve so as to approach the needle portion 30. Therefore, the distal member 68 and the distal end sleeve 65 are attached to contact the surface of the foramen ovale valve M2 at the left atrial side and hold the M2. Thereafter, while the foramen ovale valve M2 is being held as above, the main tube 63 of the positioning hold means 60 is pushed against the atrial septum secundum M1.

Subsequently, in the second lock portion R2 of the lock-unlock mechanism 102 shown in FIGS. 12 and 13, the large diameter portion 106 is pushed into the locking portion 105 which is a wedge-like through hole, whereby the operation wire 14 is locked. As a result, even if the operator loses his/her hold of the grasping member 15, the holding state is reliably maintained, and the state of holding the foramen ovale valve M2 is not loosened. Therefore, the operator can cause the needle operation lever 78 to advance by using only one hand.

(3) Temporary Grasping Process

During the temporary grasping process, the sandwiching portion operation lever 122 is operated such that the wire portions 22 having protruded from the lumens L3 and L4 is slightly pulled into the lumens L3 and L4. At this time, the action switching portion 130 has already been released, and the sandwiching portion 20 has already been able to move independently of the slide portion 100. Therefore, it is possible to operate only the wire portions 22 by using the sandwiching portion operation lever 122, without exerting influence on the main tube 63 that moves in tandem with the slide portion 100.

Then the wire portions 22 are operated so as to be slightly pulled into the lumens L3 and L4. As a result, as shown in FIG. 20, the curve of the wire portions 22 is straightened and is elastically deformed into a shape close to a straight line, and the flat plate portion 21 is pushed against the atrial septum secundum M1. By this action, the atrial septum secundum M1 is sandwiched between the flat plate portion 21 and the main tube 63. Thereafter, during the process of sandwiching the atrial septum secundum M1 between the flat plate portion 21 and the main tube 63, the rotation direction position of the catheter main body 10 that easily rotates on the axis is corrected, whereby the catheter is placed in a rotation direction position that is appropriate for the atrial septum secundum M1. In this manner, sticking or heating that will be performed later on the biological tissue M can be conducted in the intended appropriate position.

(4) Sticking Process

When the needle operation lever 78 is caused to advance in the direction of the arrow (see FIG. 14), the needle distal portions 31 of the needle portion 30 protrude from the distal end of the catheter main body 10, and as shown in FIG. 20, the needle distal portions 31 are stuck into a predetermined position of the foramen ovale valve M2. At this time, the needle distal portions 31 are formed in a state of being curved, and the lumens L1 and L2 are also formed in a state of being curved. Therefore, the two needle distal portions 31 keep protruding while expanding toward the outside (see FIG. 2).

During the sticking process, since the atrial septum secundum M1 is temporarily grasped by the flat plate portion 21, the rotation direction position of the distal portion of the catheter main body 10 has been determined appropriately for the biological tissue M. Moreover, since the foramen ovale valve M2 is held by the positioning hold means 60, the needle distal portions 31 can be rather easily stuck into an appropriate position of the foramen ovale valve M2.

Once the needle portion 30 is stuck, the position of the needle portion 30 is fixed in the relationship between the needle portion 30 and the foramen ovale valve M2. Accordingly, the operator can easily perform the process following the sticking process.

After sticking is completed, the sandwiching portion operation lever 122 is operated such that the wire portions 22 protrude from the lumen L3 and L4 toward the distal side. As a result, as shown in FIG. 21, the flat plate portion 21 is separated from the atrial septum secundum M1. At this time, by the sandwiching portion operation lever 122, the sandwiching portion 20 can be operated independently of the positioning hold means 60 and the like. Accordingly, even if the operation of separating the flat plate portion 21 from the biological tissue M is performed, other portions such as positioning hold means 60 do not move in tandem with the flat plate portion, and the determined position of the foramen ovale valve M2 can be appropriately maintained as is.

Thereafter, in the operation unit at the operator's side 70, the terminal 81 mounted on the needle operation lever 78 advances and comes into contact with the contact member 84, whereby the needle portion 30 becomes electrically conductive with the input connector 75 (see FIG. 8).

(5) Slide Portion-Moving Process

When the flat plate portion 21 is positioned to face the atrial septum secundum M1, as shown in FIG. 15(A), the slide portion 100 is caused to retract from the main body portion 71. Even at this point of time, a portion of the guide bar 88A has entered into or covers a part of the connection hole 74, whereby the output connector 87 is still hindered from being connected to the input connector 75, and safety is secured.

At this stage, by pushing the pusher piece 109 to unlock the second lock portion R2 in the lock-unlock mechanism 102 shown in FIGS. 12 and 13, and to unlock the operation wire 14, the pressure applied to the first elastic wires 66 and the second elastic wires 67 by the operation wire 14 and the distal member 68 is removed, and the first elastic wires 66 and the second elastic wires 67 are straightened due to the elastic force of their own. In this state, if the slide portion 100 is operated to retract as shown in FIG. 15, the positioning hold means 60 is taken back into the lumen L5 of the catheter main body 10 through the main tube 63 as shown in FIG. 22. As shown in FIG. 15(B), when the "OK" display portion H6 appears on the window 73, the operator sees that the positioning hold means 60 is completely taken back. Thereafter, the cutout portion 89 of the guide bar 88A matches with the connection hole 74, whereby the output connector 87 can be connected to the input connector 75 for the first time.

(6) Sandwiching Process

During the process of causing a retraction movement of the slide portion, the slide portion 100 performs the retraction movement together with the action switching portion 130. When the first engagement portion 142 moves closer to the proximal side than to the deformation inducing portion 150, as shown in FIG. 10(A), the interlock member 140 having been bent recovers its original shape. Subsequently, since the slope 144 is formed at the proximal side of the second engagement portion 143, the second engagement portion 143 smoothly goes over the terminal 83 and moves to the proximal side of the terminal 83, whereby the terminal 83 is sandwiched again between the first and second engagement portions 142 and 143. Thereafter, when the slide portion 100 is caused to retract, as shown in FIG. 10(B), the terminal 83 is pulled or moved toward the proximal side by the first engagement portion 142 of the action switching portion 130 and moves together with the slide portion 100, and the flat plate portion 21 retracts. Then when the wire portions 22 are pulled into the lumens L3 and L4, as shown in FIG. 23, the wire portions 22 are deformed and straightened. As a result, the flat plate portion 21 is attached to the atrial septum secundum M1, and the atrial septum secundum M1 and the foramen ovale valve M2 are sandwiched between the needle distal portions 31 and the flat plate portion 21.

Thereafter, in the operation unit at the operator's side 70, as shown in FIG. 10(C), the terminal 83 retracts and comes into contact with the contact member 85, whereby the sandwiching portion 20 becomes electrically conductive with the input connector 75.

In this manner, the action of the sandwiching portion 20 that has been separated by the action switching portion 130 in tandem with the retraction movement of the slide portion 100 is performed again in tandem with the movement of the slide portion 100. As a result, by only moving the slide portion 100, the positioning hold means 60 and the sandwiching portion 20 can be operated.

(7) Connection Process

At this stage, since the terminal 81 of the needle portion 30 side has become electrically conductive with the contact member 84 as described above, both the sandwiching portion 20 and the needle portion 30 can be supplied with electric energy.

Subsequently, as shown in FIG. 16, when the output connector 87 is connected to the input connector 75, power can be supplied from the energy supply means 4.

Then the switch SW is operated, whereby predetermined electric energy controlled by the control unit 5 is supplied to the sandwiching portion 20 and the needle portion 30, and the atrial septum secundum M1 and the foramen ovale valve M2 are heated.

If the tissues are continuously heated at a fusion temperature kept at a constant level, the tissues of the atrial septum secundum M1 and the foramen ovale valve M2 are melted and fused with each other due to an adhesive factor such as collagen or elastin. The control unit 5 for electric energy controls the output at a low level such that thrombi do not easily adhere to the device. Therefore, even if a portion of the sandwiching portion 20 and a portion of the needle portion 30 are exposed to the blood, it is possible to prevent thrombi from adhering to the sandwiching portion 20 or the needle portion 30.

(8) Process of Retracting from Sticking Site

After fusion is completed, the needle operation lever 78 shown in FIG. 16 is retracted and put in the state as shown in FIG. 17, and the needle portion 30 is accommodated in the distal tip 40. As a result, the terminal 81 that moves along with the needle operation lever 78 is separated from the contact member 84 (see FIG. 7), whereby the state in which electricity is applied to the clamping means K is removed. Subsequently, the output connector 87 is detached from the input connector 75. Before the needle portion 30 is caused to retract, the sandwiching portion operation lever 122 or the slide portion 100 may be operated to advance so as to cause the flat plate portion 21 to advance, and the flat plate portion 21 may be separated from the atrial septum secundum M1. In this case, after the needle portion 30 is caused to retract, the sandwiching portion operation lever 122 or the slide portion 100 is operated to retract, whereby the wire portions 22 are accommodated again into the lumens L3 and L4.

Then the push button 93 of the interlock mechanism 90 is pushed to separate the Y-connector 72 from the main body portion 71 and to separate the guiding catheter 3 from the main body portion 71, and the main body portion 71 is caused to retract so as to be separated from the living body. In this manner, the device is pulled out of the body by using the guiding catheter 3 as a guide. Thereafter, the guiding catheter 3 is removed from the living body to complete the procedure.

As described above, according to the present embodiment, the device includes the action switching portion 130 that causes the sandwiching portion 20 to advance and retract in tandem with or independently of the slide portion 100 by the advance and retraction of the slide portion 100. Therefore, by only operating the slide portion 100, the sandwiching portion 20 and the needle positioning portion 61 that act in different ways can be operated, whereby the operability is improved.

In addition, the action switching portion 130 interlocks the sandwiching portion 20 with the slide portion 100 or separates the sandwiching portion 20 from the slide portion 100 by the operation of the slide portion 100, such that the sandwiching portion 20 advances and retracts in tandem with or independently of the slide portion 100. Accordingly, it is possible to effectively cause the sandwiching portion 20 to advance and retract in tandem with or independently of the slide portion 100.

Furthermore, since the sandwiching portion 20 and the positioning hold means 60 (positioning portion) that act in different ways can be operated simply by operating a single slide portion 100, when a defect present in the biological tissue M is closed using electric currents, the operability is improved.

Moreover, since the interlock member 140 is separably interlocked with the terminal 81 (proximal member) of the sandwiching portion 20, other members do not need to be provided separately, and the action of the sandwiching portion 20 can be switched by using the terminal 81 necessary for applying electric currents.

In addition, when bumping into or contacting the deformation inducing portion 150, the interlock member 140, which moves when the slide portion 100 is pushed, is deformed and separated from the terminal 81. Consequently, the interlock member 140 can be deformed by pushing the slide portion 100, and the action of the sandwiching portion 20 can be effectively switched.

Further, when the slide portion 100 is pushed, the action switching portion 130 causes the sandwiching portion 20 to move independently in a state where both the sandwiching portion 20 and the positioning hold means 60 are advancing. Moreover, when the slide portion 100 is pulled back, the action switching portion 130 moves the sandwiching portion 20 in a state where the positioning hold means 60 is retracting, such that both the sandwiching portion 20 and the positioning hold means 60 retract. Therefore, the positioning hold means 60 operated in a wide range (in a long distance) and the sandwiching portion 20 operated in a narrow range (in a short distance) can be operated by the action of a single slide portion 100, hence the operability is improved.

In addition, since the sandwiching portion 20 is interlocked with the sandwiching portion operation lever 122, the sandwiching portion 20, which has been caused to independently advance and retract, can be individually operated, hence the operability is improved.

The invention is not limited to the aforementioned embodiment as variations can be implemented. For example, in the present embodiment, the device used for treatment for closing a defect of PFO has been described. However, the medical device is not limited in this regard, and can be used as a left atrial appendage closure device for closing a pathway-like defect or can be used in a case of causing necrosis of the biological tissue M in a predetermined site by heating. The medical device can also be applied to devices required to perform two or more types of actions in the living body even if the devices do not perform thermal treatment. For example, the medical device can be applied to devices that cause a target substance to indwell in the living body or take back the substance, devices which make an incision in biological tissues, devices for administering medicines, and the like.

Moreover, the construction of the action switching portion is not limited to the specific construction described above. For example, as shown in the modified example of the action switching portion illustrated in FIGS. 25 and 26, a member 161 which advances and retracts while being interlocked with an operation unit may be provided with an action switching portion 162 which is assembled so as to be freely pulled out and consists of telescoping tubes (axially extendable and contractable tube arrangement) forming plural steps. The member 161 is interlocked with a shaft portion 163 that advances and retracts along with the operation unit. The distal end of the action switching portion 162 is interlocked with another shaft portion 164. The distal end of the action switching portion 162 is provided with an engagement portion 165 that extends in a direction orthogonal to the direction of the advance and retraction. A case 166 accommodating the action switching portion 162 is provided with two deformation inducing portions 167 and 168 for interposing the direction of the advance and retraction of the engagement portion 165 therebetween. If the operation unit is caused to advance in this configuration, as shown in FIG. 25(A), the two shaft portions 163 and 164 move in tandem with each other until the engagement portion 165 comes into contact with the deformation inducing portion 167 at the distal side (left side in FIG. 25(A)). After the engagement portion 165 has come into contact with the deformation inducing portion 167 at the distal side, the action switching portion 162 contracts as shown in FIG. 25(B), and only the shaft portion 163 moves. Moreover, when the operation unit is caused to retract, as shown in FIG. 26(A), the two shaft portions 163 and 164 move in tandem with each other until the engagement portion 165 comes into contact with the deformation inducing portion 168 at the proximal side. After the engagement portion 165 has come into contact with the deformation inducing portion 168 at the proximal side (right side in FIG. 26), as shown in FIG. 26(B), the action switching portion 162 is stretched or expanded (extended), and only the shaft portion 163 moves. In this manner, if the action switching portion 162 has the telescoping construction, regardless if the shaft portion 164 is interlocked with or not separated from the operation unit, the shaft portion 164 can be moved in tandem with or independently of the operation unit.

In addition, in order to make the action switching expandable, an elastic member such as a spring that is stretched when coming into contact with the deformation inducing portion can be used as the action switching portion.

Further, as shown in another modified example of the action switching portion described in FIG. 27, the constituents of the action switching portion of the present embodiment may be disposed such that the front side of the action switching portion is switched with the back side of the action switching portion. That is, an action switching portion 170 includes a girder-like interlock member 172 of which the distal side (left side in FIG. 27) is interlocked with a member 171 which advances and retracts while being interlocked with an operation unit, and a deformation inducing portion 175 that is disposed at the proximal side (right side in FIG. 27) of the interlock member 172. At the proximal side of the interlock member 172, a first engagement portion 173 and a second engagement portion 174 are formed. The member 171 is interlocked with a shaft portion 176 that advances and retracts along with the operation unit. A member 177 that can be engaged with and separated from the first and second engagement portions 173 and 174 is interlocked with another shaft portion 178. With the device constructed as above, when the operation unit is caused to advance, as shown in FIG. 27(A), first, only the shaft portion 176 moves until the first engagement portion 173 moves closer to the distal side than to the deformation inducing portion 175, and the member 177 is engaged between the first and second engagement portions 173 and 174. Thereafter, as shown in FIG. 27(B), the two shaft portions 176 and 178 move in tandem with each other. Moreover, when the operation unit is caused to retract, the two shaft portions 176 and 178 move in tandem with each other until the interlock member 172 comes into contact with the deformation inducing portion 175. After the interlock member 172 comes into contact with the deformation inducing portion 175, as shown in FIG. 27(C), the interlock member 172 is deformed, and the member 177 escaped from the position between the first and second engagement portions 173 and 174, whereby only the shaft portion 176 moves.

The device may include three or more shaft portions moved by the operation unit. Moreover, the device may have a structure in which two or more shaft portions advance and retract in tandem with or independently of the operation unit.

In the present embodiment, the taper surface 151 is formed in the deformation inducing portion 150. However, a taper surface may be formed at the distal end of the interlock member 140 or may not be formed in both the deformation inducing portion 150 and the interlock member 140. Moreover, the slope 144 may not be formed in the second engagement portion 143.

The detailed description above describes embodiments of a medical device representing examples of the medical device disclosed here. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device positionable in a living body to correct a defect in biological tissue in the living body, the medical device comprising:
    a catheter main body configured to be inserted into the living body;
    a clamp to clamp a portion of the biological tissue, the clamp including a needle configured to puncture the biological tissue and a sandwiching member that, together with the needle, sandwiches the portion of the biological tissue;
    an elongated tube positioned in the catheter main body and axially movable relative to the catheter main body;
    an operation unit including an operation unit main body portion that is fixed to the catheter main body and an operation unit slide portion that is manually operable to undergo axial movement, the operation unit slide portion being fixed directly to the elongated tube so that the elongated tube moves together with the operation unit slide portion relative to the catheter main body whenever the operation unit slide portion axially moves relative to the catheter main body and the operation unit main body portion through manual operation of the operation unit slide portion;
    an operation wire which is axially movable relative to the operation unit slide portion and passes through the elongated tube and through the operation unit, the operation wire including a positioning hold member at a distal end of the operation wire;
    an action switching portion operatively located between the operation unit slide portion and the sandwiching member, the action switching portion being configured to movably link the operation unit slide portion and the sandwiching member so that the sandwiching member is constrained to move together with the operation unit slide portion relative to the catheter main body for a predetermined distance during the axial movement of the operation unit slide portion, the action switching portion being configured to separate the operation unit slide portion from the sandwiching member on a distal side relative to a first moving range of the operation unit slide portion relative to the operation unit main body portion in which the operation unit slide portion axially moves together with the sandwiching member so that, in a second moving range of the operation unit slide portion distal of the first moving range relative to the operation unit main body portion, the operation unit slide portion axially moves independently of the sandwiching member and independently of the catheter main body;
    a first lock-unlock mechanism for releasably interlocking the operation unit main body portion and the operation unit slide portion to prevent the operation unit slide portion from sliding relative to the operation unit main body portion; and
    a second lock-unlock mechanism for releasably interlocking the operation wire and the operation unit slide portion to prevent the operation wire from sliding relative to the operation unit slide portion.

2. The medical device according to claim 1, wherein the sandwiching member is a flat plate member possessing a proximal end which is connected to a wire portion, the wire portion possesses a curved distal portion.

3. The medical device according to claim 1, further comprising a plurality of wires each possessing one end fixed to a distal end portion of the elongated tube and possessing an opposite end fixed to an intermediate sleeve.

4. The medical device according to claim 3, wherein the operation wire passes through the intermediate sleeve.

5. The medical device according to claim 1, wherein the positioning hold member comprises an enlarged distal member at the distal end of the operation wire.

6. The medical device according to claim 1, wherein the action switching portion includes an interlock member provided with an engagement portion that engages a proximal end portion of the sandwiching member so that the sandwiching member moves together with the operation unit slide portion during the axial movement of the operation unit slide portion.

7. The medical device according to claim 6, wherein the action switching portion also includes a deformation inducing portion that is contacted by the interlock member to induce deformation of the interlock member that causes the engagement portion to release the proximal end portion of the sandwiching member so that the operation unit slide portion axially moves independent of the sandwiching member.

8. The medical device according to claim 7, wherein the interlock member moving in a first axial direction is deformed by contact with the deformation inducing portion, and the deformation inducing portion is configured to release the deformation of the interlock member when the interlock member moving in a second axial direction opposite the first axial direction moves out of contact with the deformation inducing portion.

9. The medical device according to claim 8, wherein the engagement portion is configured so that when the interlock member moving in the second axial direction moved out of contact with the deformation inducing portion, the engagement portion engages the proximal end portion of the sandwiching member so that the sandwiching member moves together with the operation unit slide portion during the axial movement of the operation unit slide portion.

10. A medical device comprising:
    a cylindrical body configured to be inserted into a living body;
    at least two shaft portions movably positioned in the cylindrical body and configured to move relative to the cylindrical body to undergo advancing and retracting movement;
    an operation unit including an operation unit main body portion that is fixed to the cylindrical body and an operation unit slide portion configured to operate the at least two shaft portions such that the operation unit slide portion and the shaft portions are constrained to advance and retract simultaneously relative to the cylindrical body and the operation unit main body portion;

an operation wire which is axially movable relative to the operation unit slide portion and passes through the operation unit and the cylindrical body, the operation wire including a positioning hold member at a distal end of the operation wire;

a first lock-unlock mechanism for releasably interlocking the operation unit main body portion and the operation unit slide portion to prevent the operation unit slide portion from advancing and retracting relative to the operation unit main body portion;

a second lock-unlock mechanism for releasably interlocking the operation wire and the operation unit slide portion to prevent the operation wire from advancing and retracting relative to the operation unit slide portion; and an action switching portion configured to make at least one of the shaft portions, on a distal side relative to a first moving range of the at least one of the shaft portions relative to the operation unit main body portion in which the at least one of the shaft portions advances and retracts in tandem with the advance and retraction of the operation unit slide portion, to, in a second moving range of the at least one of the shaft portions distal of the first moving range relative to the operation unit main body portion, advance and retract relative to the cylindrical body independently of the advance and retraction of the operation unit slide portion, wherein the action switching portion includes an interlock member connected to and movable together with the operation unit slide portion, the interlock member being separably interlockable with a proximal member of the at least one of the shaft portions so that in an interlocked state the interlock member and the proximal member are interlocked with one another and move together, and in a separate state the interlock member and the proximal member are separate from one another and independently movable relative to one another.

11. The medical device according to claim 10, wherein the action switching portion interlocks at least one of the shaft portions with the operation unit slide portion so that the at least one shaft portion and the operation unit slide portion move together, and wherein the action switching portion separates the at least shaft portion from the operation unit slide portion so that the at least one shaft portion and the operation unit slide portion move independently of one another.

12. The medical device according to claim 10, further comprising a needle portion configured to be stuck into biological tissue in a vicinity of a defect in the biological tissue, the needle part being connectable to an electric source so that the needle portion functions as an electrode that applies electric current to the biological tissue;

the at least one of the shaft portions that advances and retracts in tandem with and independently of the operation unit slide portion by the action switching portion is a sandwiching portion that sandwiches the biological tissue between the sandwiching portion and the needle portion, the sandwiching portion being connectable to the electric source so that the sandwiching portion functions as an electrode that applies electric current to the biological tissue sandwiched between the sandwiching portion and the needle portion; and the other shaft portion that is not the sandwiching portion is a positioning portion which is configured to be brought into contact with the biological tissue to help position at least one of the needle portion and the sandwiching portion in the biological tissue.

13. The medical device according to claim 12, wherein the sandwiching portion includes a sandwiching shaft possessing a distal portion positionable at a position protruding distally beyond the cylindrical body and the proximal member, the proximal member being disposed at a proximal end of the sandwiching shaft and movable into contact with a contact member to supply the electric current.

14. The medical device according to claim 13, wherein the action switching portion includes a deformation inducing portion that deforms the interlock member by contacting the interlock member, which moves by a push-in operation of the operation unit slide portion, to separate the interlock member from the proximal member.

15. The medical device according to claim 12, wherein the action switching portion causes the sandwiching portion to independently move in a state where both the sandwiching portion and the positioning portion advance, by a push-in operation of the operation unit slide portion, and causes the sandwiching portion to move in tandem with the retracting positioning portion in a state where the positioning portion is retracting by a pull-back operation of the operation unit slide portion such that both the sandwiching portion and the positioning portion retract.

16. The medical device according to claim 10, wherein the at least one of the shaft portions, which advances and retracts in tandem with and independently of the operation unit slide portion by the action switching portion, is movable in an advancing and retracting manner by an operation member different from the operation unit slide portion.

17. A method of operating a device positionable in a living body to correct a defect in biological tissue in the living body, the method comprising:

positioning the medical device in the living body, the medical device comprising: a catheter main body configured to be inserted into the living body; a clamp to clamp a portion of the biological tissue, the clamp including a sandwiching portion; an elongated tube positioned in the catheter main body and axially movable relative to the catheter main body; an operation unit including an operation unit main body portion that is fixed to the catheter main body and an operation unit slide portion that is fixed directly to the elongated tube and is manually operable to undergo axial movement relative to the operation unit main body portion and the catheter main body; an operation wire which axially moves relative to the operation unit slide portion passes through the operation unit and the elongated tube, the operation wire including a positioning hold member at a distal end of the operation wire; a first lock-unlock mechanism for releasably interlocking the operation unit main body portion and the operation unit slide portion to prevent the operation unit slide portion from undergoing axial movement relative to the operation unit main body portion; and a second lock-unlock mechanism for releasably interlocking the operation wire and the operation unit slide portion to prevent the operation wire from undergoing axial movement relative to the operation unit slide portion;

axially moving in a distal direction, relative to the catheter main body, the operation unit slide portion, which is operatively connected to both the sandwiching portion and the elongated tube such that they are constrained to move together relative to the catheter main body, to axially move both the sandwiching portion and the elongated tube together with the operation unit slide portion relative to the catheter main body and the operation unit main body portion;

disconnecting the operative connection between the operation unit slide portion and the sandwiching portion while maintaining the operative connection between the operation unit slide portion and the elongated tube at the end of the axial movement in the distal direction of the operation unit slide portion; and further axially moving the operation unit slide portion relative to the catheter main body and the operation unit main body portion after the operative disconnection of the sandwiching portion from the operation unit slide portion so that the further axial movement of the operation unit slide portion axially moves the elongated tube relative to the catheter main body without axially moving the sandwiching portion relative to the catheter main body.

18. The method according to claim 17, wherein the operation unit slide portion is operatively connected to the sandwiching portion by an interlock member, the operative disconnection of the operation unit slide portion from the sandwiching portion comprising contacting the interlock member with a deformation inducing portion that deforms the interlock member.

19. The method according to claim 17, wherein the operation unit slide portion is operatively connected to the sandwiching portion by an axially extendable and contractible tube arrangement, the operative disconnection of the operation unit slide portion from the sandwiching portion comprising contacting a part of the axially extendable and contractible tube arrangement with a deformation inducing portion that causes the axially extendable and contractible tube arrangement to contract during the axial movement of the operation unit slide portion.

20. The method according to claim 17, further moving the sandwiching portion into contact with the biological tissue and supplying electric energy to the sandwiching portion to cause fusion or necrosis of the biological tissue.

* * * * *